US011363941B2

(12) United States Patent
Kaffes et al.

(10) Patent No.: US 11,363,941 B2
(45) Date of Patent: Jun. 21, 2022

(54) CHOLANGIOSCOPY OVERTUBE AND ENDOSCOPE ASSEMBLY

(71) Applicants: Micro-Tech (Nanjing) Co., Ltd., Nanjing (CN); Arthur John Kaffes, Bellevue Hill (AU)

(72) Inventors: Arthur John Kaffes, Bellevue Hill (AU); Changqing Li, Nanjing (CN); Chunxia Shi, Nanjing (CN); Jianyu Wei, Nanjing (CN); Zhenghua Shen, Nanjing (CN)

(73) Assignees: MICRO-TECH (NANJIN) CO., LTD., Nanjing (CN); John Arthur Kaffes, Bellevue Hill (AU)

( * ) Notice: Subject to any disclaimer, the term of this patent is extended or adjusted under 35 U.S.C. 154(b) by 10 days.

(21) Appl. No.: 16/910,947

(22) Filed: Jun. 24, 2020

(65) Prior Publication Data
US 2020/0405128 A1   Dec. 31, 2020

Related U.S. Application Data

(60) Provisional application No. 62/952,531, filed on Dec. 23, 2019, provisional application No. 62/868,421, filed on Jun. 28, 2019.

(51) Int. Cl.
*A61B 1/00* (2006.01)
*A61B 1/005* (2006.01)
(Continued)

(52) U.S. Cl.
CPC ........ *A61B 1/00135* (2013.01); *A61B 1/0008* (2013.01); *A61B 1/0052* (2013.01);
(Continued)

(58) Field of Classification Search
None
See application file for complete search history.

(56) References Cited

U.S. PATENT DOCUMENTS

| 8,486,010 | B2 | 7/2013 | Nomura |
| 10,561,818 | B2 | 2/2020 | Cole et al. |
(Continued)

FOREIGN PATENT DOCUMENTS

| CN | 102413863 A | 4/2012 |
| CN | 102727156 A | 10/2012 |
(Continued)

OTHER PUBLICATIONS

Chinese International Search Report for International Application No. PCT/CN2020/098137, dated Aug. 17, 2020, 6 pages.

*Primary Examiner* — Timothy J Neal
(74) *Attorney, Agent, or Firm* — Mai-Tram D. Lauer; Westman, Champlin & Koehler, P.A.

(57) ABSTRACT

An overtube device and an endoscope assembly are provided, the overtube device includes an overtube body having a proximal end and a distal end, the overtube body is provided with a bore which extending from the distal end to the proximal end of the overtube body, the bore is configured to allow a passing portion of the endoscope assembly to pass therethrough; a pulling lumen is formed in the overtube body, which extends from the distal end to the proximal end of the overtube body, the pulling lumen is configured to allow a pulling part to pass therethrough, and the distal end of the pulling part is fixed with the distal end of the overtube body.

29 Claims, 9 Drawing Sheets

(51) Int. Cl.
*A61M 25/10* (2013.01)
*A61B 1/05* (2006.01)
*A61M 25/00* (2006.01)
*A61B 1/273* (2006.01)
*A61M 25/01* (2006.01)

(52) U.S. Cl.
CPC ...... *A61B 1/00073* (2013.01); *A61B 1/00137* (2013.01); *A61B 1/00154* (2013.01); *A61B 1/05* (2013.01); *A61B 1/2736* (2013.01); *A61M 25/0053* (2013.01); *A61M 25/0133* (2013.01); *A61M 25/10* (2013.01); *A61B 1/0057* (2013.01)

(56) References Cited

U.S. PATENT DOCUMENTS

| | | | | |
|---|---|---|---|---|
| 2003/0216615 | A1* | 11/2003 | Ouchi | A61B 1/00078 600/121 |
| 2004/0138529 | A1* | 7/2004 | Wiltshire | A61B 1/0055 600/144 |
| 2005/0222581 | A1* | 10/2005 | Fischer, Jr. | A61B 1/00135 606/108 |
| 2006/0015006 | A1* | 1/2006 | Laurence | A61B 1/00135 600/104 |
| 2008/0262294 | A1* | 10/2008 | Ewers | A61B 1/00105 600/104 |
| 2008/0262301 | A1* | 10/2008 | Gibbons | A61B 1/01 600/114 |
| 2010/0256446 | A1* | 10/2010 | Raju | A61B 1/018 600/114 |
| 2011/0230718 | A1 | 9/2011 | Akui | |
| 2012/0265132 | A1 | 10/2012 | Nomura | |
| 2013/0041214 | A1* | 2/2013 | Maahs | A61B 1/05 600/104 |
| 2013/0281781 | A1* | 10/2013 | Farhadi | A61B 1/00094 600/116 |
| 2014/0024897 | A1* | 1/2014 | Inoue | A61B 1/00154 600/115 |
| 2014/0088355 | A1* | 3/2014 | Schaeffer | A61B 17/24 600/109 |
| 2017/0368304 | A1 | 12/2017 | Cole et al. | |
| 2018/0184886 | A1 | 7/2018 | Sugimoto et al. | |

FOREIGN PATENT DOCUMENTS

| | | |
|---|---|---|
| CN | 103096964 A | 5/2013 |
| CN | 107206204 A | 9/2017 |
| CN | 109799604 A | 5/2019 |
| WO | 2017090133 A1 | 6/2017 |

* cited by examiner

FIG. 8

CHOLANGIOSCOPY OVERTUBE AND ENDOSCOPE ASSEMBLY

CROSS-REFERENCE TO RELATED APPLICATIONS

The present application claims priority of U.S. provisional patent application No. 62/868,421, entitled "Cholangioscopy Overtube" and filed with the USPTO on Jun. 28, 2019 and priority of U.S. provisional patent application No. 62/952,531, entitled "Cholangioscopy Overtube" and filed with the USPTO on Dec. 23, 2019, the contents of both of which are incorporated herein by reference in their entireties.

TECHNICAL FIELD

The present disclosure relates to the technical field of medical devices and in particular to an overtube device and an endoscope assembly thereof.

BACKGROUND INFORMATION

In minimally invasive interventional diagnosis and treatment, medical overtubes (or sheaths) are mainly used for building channels, conveying or retrieving medical devices, injection medicines and exporting body fluids, etc. A doctor can perform operations by using existing instruments such as overtube balloons, snares, balloon catheters, guiding probes, etc. and extending them into the body of a patient via overtubes.

SUMMARY

In a first aspect, an embodiment of the present disclosure provides an overtube device comprising:
   a overtube body having a proximal end and a distal end, wherein the overtube body has an outer surface and an inner surface that defines a bore extending along a longitudinal axis;
   a thickness of the overtube body measured radially relative to the longitudinal axis between the outer surface and an inner surface;
   a first pulling lumen formed in the overtube body between the inner surface and the outer surface, wherein the first pulling lumen has a diameter smaller than a diameter of the bore;
   wherein the first pulling lumen is adapted to receive a component therein that effectuates movement of the overtube body at the distal end such that the overtube device may be installed over a passing portion of an endoscope body to structurally support the passing portion.

In a second aspect, an embodiment of the present disclosure provides an endoscope assembly comprising:
   an endoscope body having a passing portion extending to a distal end, wherein the endoscope body has a sensor adjacent the distal end of the passing portion to capture images or video;
   an overtube defining a bore, wherein the passing portion of the endoscope body is positioned within the bore;
   wherein the overtube is adapted to structurally support the passing portion of the endoscope body during a medical procedure.

In a third aspect, an embodiment of the present disclosure provides an overtube device, comprising:
   a overtube body having a proximal end and a distal end, wherein the overtube body is provided with a bore extending in a direction from the distal end of the overtube body to the proximal end of the overtube body, and the bore is configured to allow a passing portion of the endoscope body to pass therethrough;
   a pulling lumen formed in the overtube body extending in the direction from the distal end of the overtube body to the proximal end of the overtube body, and the pulling lumen is configured to allow a pulling part to pass therethrough, a distal end of the pulling part is fixed with a distal portion of the overtube body such that the distal portion of the overtube body and the passing portion within the distal portion are bent and/or moved together when the pulling part moves towards the proximal end of the overtube body.

In a fourth aspect, an embodiment of the present disclosure provides an endoscope assembly, comprising an endoscope body and the overtube device as described in the foregoing third aspect, wherein the passing portion of the endoscope body can slidably pass through the bore.

BRIEF DESCRIPTION OF THE SEVERAL VIEWS OF THE DRAWINGS

A sample embodiment of the disclosure is set forth in the following description, is shown in the drawings and is particularly and distinctly pointed out and set forth in the appended claims. The accompanying drawings, which are fully incorporated herein and constitute a part of the specification, illustrate various examples, methods, and other example embodiments of various aspects of the disclosure. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

FIG. 8 is a schematic view of the second overtube device viewed from a first angle of view;

Figure 1:
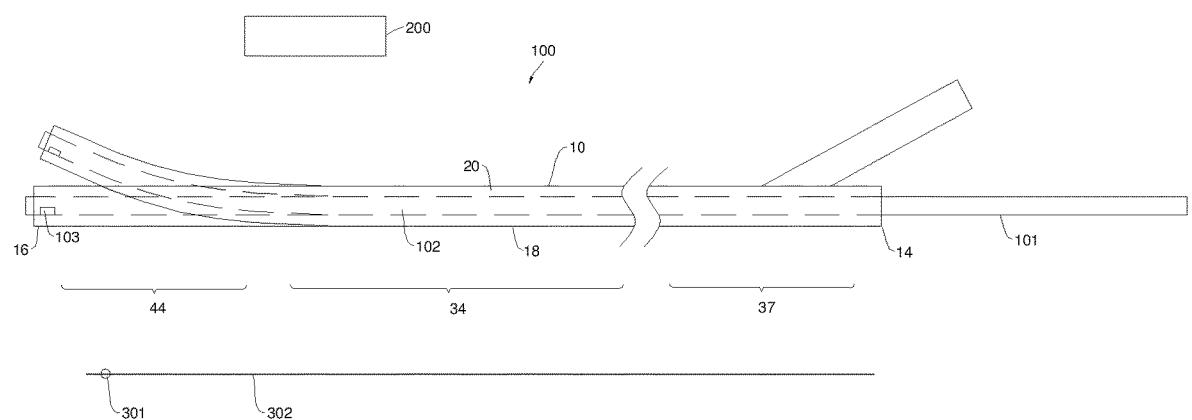
FIG. 1 is a schematic view of an endoscope assembly provided in an embodiment of the present disclosure.

Reference signs: 10—overtube device; 12—operation part; 120—first finger ring; 121—ratchet; 14—proximal end; 15—passage hole; 16—distal end; 17—distal transparent cap; 171—air hole; 18—overtube body; 181—braided catheter; 182—tube body; 183—braided catheter structure; 20—bore; 21—installation part; 22—barrel; 221—mounting port; 222—medical tube; 223—communication hole; 224—Luer connector; 24—connector; 241—mounting port; 26—handle; 261—sliding body; 262—button; 263—pawl; 264—second ring; 265—shaft; 266—elastic piece; 28—longitudinal axis; 32—shoulder; 34—intermediate portion; 35—midline; 36—groove; 36A—first groove; 36B—second groove; 36C—third groove; 37—proximal portion; 371—guide hole; 38—first ring; 40—opening; 42—edge; 44—distal portion; 441—flexible film; 45—distal hole; 46—second ring; 48—pulling lumen; 48A—first pulling lumen; 48B—second pulling lumen; 48C—third pulling lumen; 48D—fourth pulling lumen; 50—outer surface; 52—inner surface; 54—pulling part; 54A—first wire; 54B—second wire; 54C—third wire; 54D—fourth wire; 56—first plane; 58—second plane; 60—sealing part; 100—endoscope assembly; 101—endoscope body; 102—passing portion; 103—sensor; 200—viewing device; 301—balloon; 302—balloon catheter.

DETAILED DESCRIPTION

It is to be noted that like numbers and letters denote like items in the following figures, therefore once an item is defined in one, it is no longer necessary to further define or explain the same in the following figures in the subsequent figures. Meanwhile, like numbers denote similar parts in all the figures.

Cholangioscopy is primarily used for the treatment of difficult bile duct stones and the evaluation of biliary strictures. Further, tumors of the biliary tract can usually be diagnosed by conventional cholangiography, either via endoscopic retrograde cholangio-pancreatography (ERCP) or percutaneous transhepatic cholangiography (PTC).

A doctor may choose to perform a cholangioscopy in the event that X-ray imaging from an endoscopic retrograde cholangiopancreatography is insufficient to make an adequate diagnosis or therapeutic intervention requires direct visualization. Using a single-operator cholangioscopy, the doctor should be able to visualize and to examine the biliary, hepatic (liver), and pancreatic ducts.

Duodenoscopes are flexible, lighted tubes that are threaded through the mouth, throat, and stomach into the top of the small intestine (duodenum). They are used during ERCP. Duodenoscopes are complex instruments that contain many small working parts. An exemplary duodenoscope defines in interior channel or passageway, which is sometimes referred to as a working channel.

A choledochoscope may extend through the working channel of duodenoscope and enter into a biliary tract. There are some shortcomings of conventional choledoschoscopes. Namely, a choledochoscope is a disposable product and is thus expensive for patients who must purchase (or be assessed the cost) of a new choledoschope for each procedure. An additional shortcoming is that the diameter of the choledochoscope must be small enough to enter into the duodenoscope. Thus, the working channel (about 1.2 mm) of the duodenoscope is small, which in turn makes the cholendochoscope even smaller. The small diameters make it difficult to manufacture these devices with sufficient strength that they may be easily controlled by the operator.

In another example, some doctors use an ultrathin gastroscope, which is used to enter into the stomach through the nose, instead of choledochoscope to enter the biliary tract. Some doctors believe there are advantages of ultrathin gastroscope being used instead of choledochoscope because the ultrathin gastroscope is a reusable product, and the ultrathin gastroscope is thicker than choledochoscope, so the ultrathin gastroscope has thicker working channel (2.0 mm), and a common diameter device can be used. This imparts a lower cost to the patient since many these components are reusable.

This is not to say that the ultrathin gastroscope is not shortcomings. The shortcomings of the ultrathin gastroscope being used instead of choledochoscope include the fact that ultrathin gastroscopes are too soft to enter the biliary tract directly. Doctors will use existing instruments, such as overtube balloon, snare, balloon catheter, guide probes, or the like to guide ultrafine gastroscopes to go into the biliary tract, which is inconvenient to use. The various surgical instruments (endoscopes) above mentioned, such as the choledochoscope, the duodenoscope and the gastroscope more or less have certain deficiencies which cause inconvenience during an operation.

An overtube (or sheath) device provided in an embodiment of the present disclosure can facilitate entering of relevant surgical instruments, for example, the endoscope in the prior art.

Referring to FIG. 1, an endoscope assembly provided in an embodiment of the present is shown in FIG. 1, the endoscope assembly 100 includes an overtube device 10 and an endoscope body (or medical viewing device) 101, wherein the overtube device 10 is provided with a bore 20, and a passing portion (or elongated portion) 102 of the endoscope body 101 may pass through the bore 20. A sensor 103 at a distal end of the passing portion 102 can capture images or video via the distal end of the overtube device 10, such that a doctor can clearly see an actual status of the corresponding area. When the passing portion 102 passes through the bore 20 of the overtube device 10, the overtube device 10 can provides greater strength and stiffness to support the passing portion 102, such that the ultra-thin elongated portion of the endoscope can be inserted through the biliary tract or biliary duct. In general, the status of the above mentioned instruments may be observed by a viewing device, such that the doctor can timely acquire real-time information. In FIG. 1, the endoscope assembly 100 further includes a balloon catheter 302 and a balloon 301 connected with the balloon catheter 302, wherein the balloon 301 and the balloon catheter 302 are configured to assists in pulling the overtube body 18. In an operation mode, the overtube body 18 is first sleeved on the endoscope body 101, and the both are together put down into the stomach, the endoscope body 101 can be directly pass through the pylorus, but usually cannot drive the overtube body 18 to pass through the pylorus. At this time, a guide wire of 0.89 mm can pass through a channel of the endoscope body 101, the guide wire is left at the duodenum, the endoscope body 101 is withdrawn, then the balloon 301 and the balloon catheter 302 are put down along the guide wire, when the balloon 301 arrives at the position of the duodenum, the balloon 301 is expanded and fixed. The overtube body 18 passes through the pylorus under the assistance of the balloon catheter 302 and reaches the duodenum, then the pressure in the balloon catheter 301 is depressurized, the balloon catheter 302 is withdrawn, the endoscope body 101 is made to reach the duodenum again along the overtube body 18, and then the endoscope body 101 enters the biliary duct under the support and assistance from the overtube body 18 for performing the operation.

With reference to FIG. 1, it is to be noted that terms "distal end" and "proximal end", etc. throughout the full text need to be explained, the explanation herein is merely for better understanding of the present disclosure, and thus should not be construed as limitations on the present disclosure. Generally, during usage of the overtube device, a front end portion (which refers to the left end of the overtube device according to relative positions in FIG. 1) of the overtube device 10 may extend into a human body, while a rear end portion (which refers to the right end of the overtube device according to relative positions in FIG. 1) of the overtube device 10 is to be kept outside the body for facilitating medical personnel's operations. For this reason, "distal end" can be understood as a front part of an element or a part that is relatively closer to the interior of the body, and "proximal end" can be understood as a rear end of an element or a part that is relatively closer to the exterior of the body. However, if the "proximal end" or "distal end" of an element or a part is not clearly indicated, by default it refers to the proximal end or the distal end of the entire overtube device 10, or the proximal end or the distal end of the entire endoscope body 101.

The overtube device 10 and the endoscope assembly 100 including the overtube device 10 provided in embodiments of the present disclosure will be described in detail below.

Figure 2:
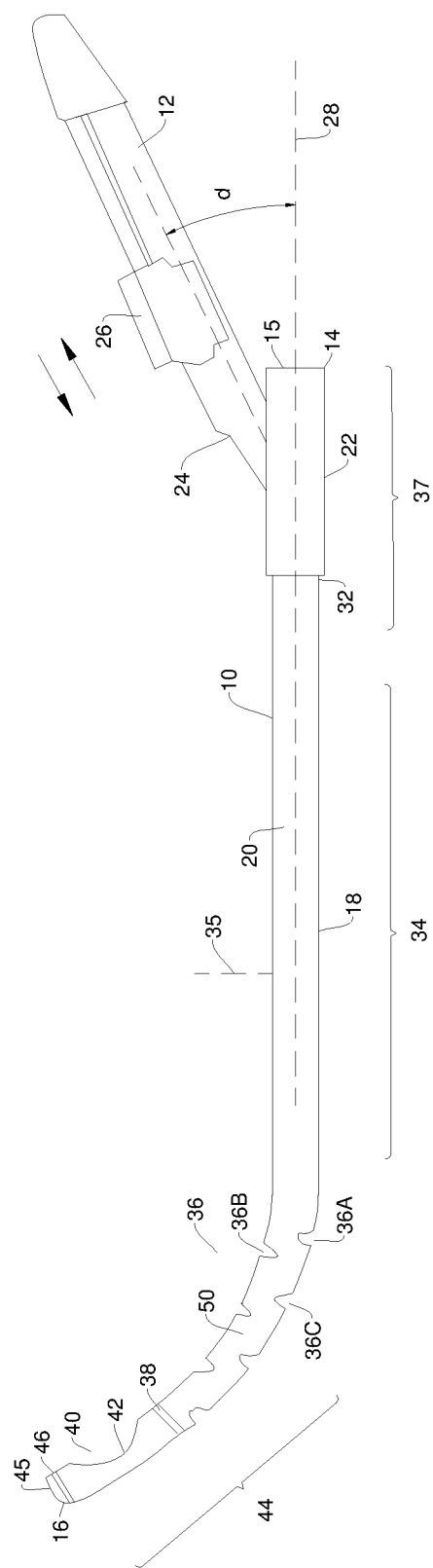
FIG. 2 is an overall view of a first overtube device provided in an embodiment of the present disclosure.

FIG. 2 depicts a first overtube 10 provided in an embodiment of the present disclosure, including an overtube body 18 having a proximal end 14 and a distal end 16. The overtube body 18 of overtube device 10 extends from the proximal end 14 to the distal end 16. The overtube body 18 may define an interior bore 20, wherein the bore 20 is configured to receive therein the passing portion 102 of the endoscope body 101. In an embodiment, the overtube body 18 is more rigid than the passing portion 102 of the endoscope body 101.

The proximal end 14 may be provided with a widened cylindrical barrel 22, wherein the barrel 22 is connected with a connector 24 that is configured to receive a handle 26. The connector 24 and the barrel 22 have a greater external diameter than the overtube body 18 of overtube device 10.

In an embodiment, connector 24 is the offset at an angle relative to a longitudinal axis 28 of the overtube body 18 of overtube device 10. More particularly, the connector 24 is angled at an included angle d, i.e., 30° relative to the longitudinal axis 28. It is to be noted that the angle d at which the connector 24 is offset relative to the longitudinal axis 28 may be any angle that would comfortably accommodate grasping of the handle 26. In some embodiments, the angle d may be in a range from about 15° to about 75°. In a more particular embodiment, the angle d may be in a range from about 25° to about 55°. For example, the angled may be any one of 15°, 25°, 30°, 40°, 45°, 55°, 75°, etc.

The barrel 22 terminates at a shoulder 32 and narrows to define the outer diameter of the overtube body 18. The overtube body 18 extends in a generally linear manner between the shoulder 32 and an intermediate portion 34. The intermediate portion 34 may be, but is not required to be, at or near a midline 35 or intermediate portion of overtube body 18. As shown in FIG. 1, the intermediate portion 34 is located distally from midline 35. Thus, intermediate portion 34 refers to a portion that is simply between the proximal end 14 and the distal end 16. The midline 35 refers to a point or line that is halfway between the proximal end 14 and the distal end 16, wherein the midline 35 is denoted by the dashed line in FIG. 2.

As shown in FIG. 2, the overtube body 18 may define a plurality of grooves 36 formed in the outer surface 50 of the overtube body 18 of the overtube device 10. The grooves 36 are located between the intermediate portion 34 and a first ring 38, which is located distally from the intermediate portion 34. In an embodiment, the grooves 36 extend at least partially around the circumference of the overtube body 18 of overtube device 10. In an embodiment, the grooves 36 may extend fully around the entire circumference of overtube body 18. When the grooves 36 do not extend fully around the circumference of overtube body 18, the grooves 36 may be staggered and offset from each other so as to enable bending of a distal portion 44 of the overtube body 18. The staggered or offset grooves 36 are provided in an alternate manner on each respective side of the overtube body 18 of overtube device 10. For example, the grooves 36 may include a first groove 36A, a second groove 36B and a third groove 36C, wherein the first groove 36A may be located on a first side of the overtube body 18 and the second groove 36B is located on an opposite side of the overtube body 18 of overtube device 10 at a position more distal from the first groove 36A. The third groove 36C may be located on the same side of the overtube body 18 of overtube device 10 as the first groove 36A more distally from the second groove 36B. Such or similar groove pattern or configuration continues until the plurality of grooves 36 end at, or shortly before, the first ring 38. The grooves 36 may be formed manufacturing and processing to be in form of recesses, or the grooves 36 may have a complete structure and are formed by cutting. It should be noted that the sizes of the grooves 36 varies with the angle and depth of cutting and the like. The grooves 36 may also be called as recesses, notches, etc.

The first ring 38 may extend fully around the circumference of outer surface 50 of overtube body 18 of overtube device 10. In an embodiment, the first ring 38 may be fabricated from a metal, that is, the first ring is a metal ring, so as to make this portion (i.e, the first ring 38) of the overtube device 10 clear and visible under a CT scan. While this embodiment envisions that the first ring 38 will be fabricated from a metal, any material could be utilized that would make itself visible under a visual inspection or another identification manner, such as an x-ray.

The overtube body 18 defines a radially aligned opening (or side hole) 40, wherein the opening 40 is located distally from the first ring 38. The radially aligned opening 40 is defined by an edge 42 that is elongated relative to the longitudinal axis 28. The opening 40 is a through opening that is in open communication with the bore 20 of the overtube body 18 of the overtube device 10, such that the opening 40 extends fully through the thickness of the sidewall of overtube body 18. The distal portion 44 of the overtube body 18 is located distally from edge 42. The distal portion 44 of the overtube body 18 extends to the terminal end of the overtube body 18, which defines the distal end 16 of the overtube device 10. A distal hole 45 may be defined by a generally circular edge at the distal end 16 of overtube device 10.

As described in greater detail herein, at least one (metal) wire, or a plurality of (metal) wires, may be embedded in the overtube body 18 of overtube device 10, which will allow an operator to grasp the handle 26 to bend the distal portion 44 of the overtube body 18 relative to the longitudinal axis 28. The bending of the distal portion 44 of the overtube body 18 is accomplished by tightening, loosening/slackening, or otherwise manipulating one of the wires to cause the distal end 16 to bend in a desired direction. The plurality of grooves 36 effectuate and enable the overtube body 18 to bend in a desired direction. The ability to bend the distal portion 44 of the overtube body 18 of the overtube device 10 enables an operator to guide or position the overtube body 18 to allow the endoscope body 101 to enter a biliary tract or duct while the sensor 103 of the endoscope body 101, such as a camera, can capture images or video through the opening 40 so that the biliary tract may be inspected by the operator.

Figure 3:
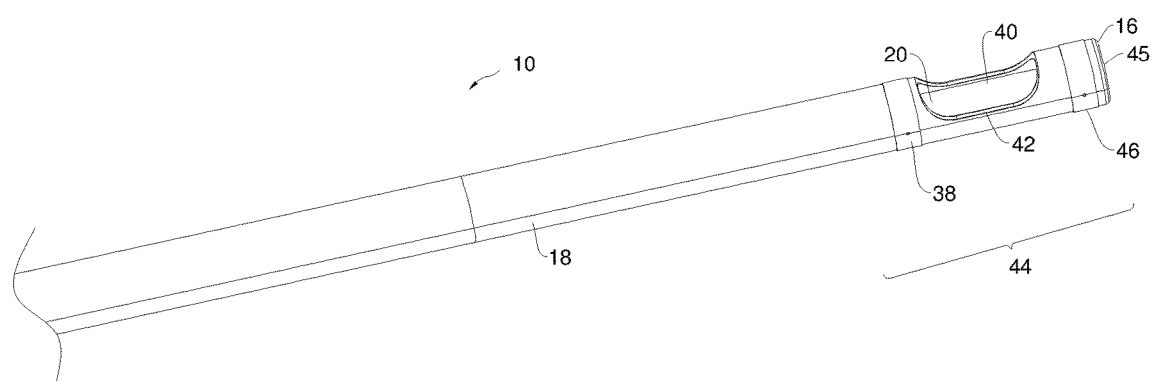
FIG. 3 is a schematic view of the first overtube device viewed from a first angle of view.

FIG. 2 and FIG. 3 in combination clearly depict the distal end 16 of the overtube device 10. In this embodiment, the distal portion 44 is covered by a second ring 46, wherein the second ring 46 may also be formed of a metal material, however, it is not required. The second ring 46 provides structural rigidity to the distal end 16 of overtube device 10 to support the passing portion 102 of the endoscope body 101, with the passing portion 102 extending through the bore 20 and a portion thereof (for example, the sensor 103) is exposed outwardly through the radial opening 40.

Figure 4:
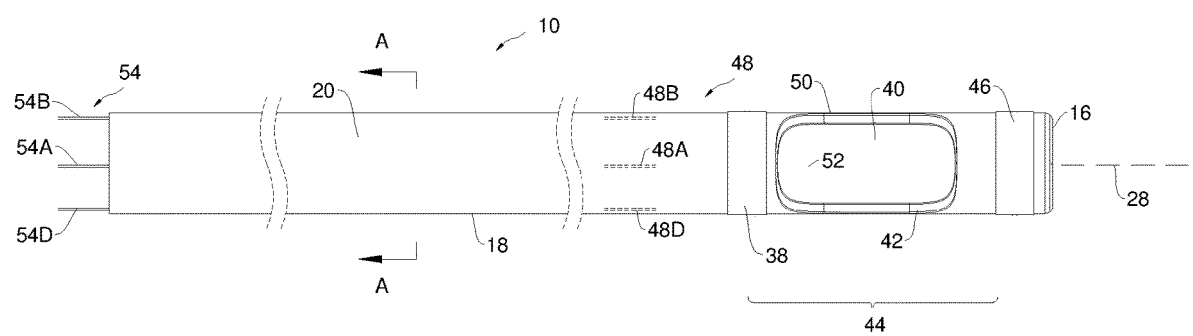
FIG. 4 is a schematic view of the first overtube device viewed from a second angle of view.

With continued reference to FIG. 4, the overtube body 18 may further define a narrow pulling lumen 48 that is formed in between the outer surface 50 and the inner surface 52 of the overtube body 18. Thus, the diameter of pulling lumen 48 is significantly narrower than the bore 20 of the overtube body 18. Because the pulling lumen 48 is disposed between the outer surface 50 and the inner surface 52, at least one wire (or pulling part) 54 may be positioned within the pulling lumen 48 to control the bending or flexing of the distal end 16 of the overtube device 10. It can be understood that the pulling lumen 48 is adapted to receive therein a component (the pulling part 54) realizing motion of the overtube body 18 at the distal end 16, such that the overtube device sleeves the passing portion 102 of the endoscope body 101, thereby structurally supporting the passing portion 102. Meanwhile, the inner surface 52 defines the bore 20 extending centrally along the longitudinal axis.

It should be noted that the pulling lumen 48 may be formed inside or outside the overtube body 18, or may be formed on an outer wall of the overtube body 18. For example, a groove may be formed on the outer wall of the overtube body 18 to form the pulling lumen, wherein the pulling part 54 may be accommodated in the groove.

Figure 5:
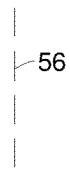
FIG. 5 is a cross section view of FIG. 4 in a direction of A-A.
Figure 5:
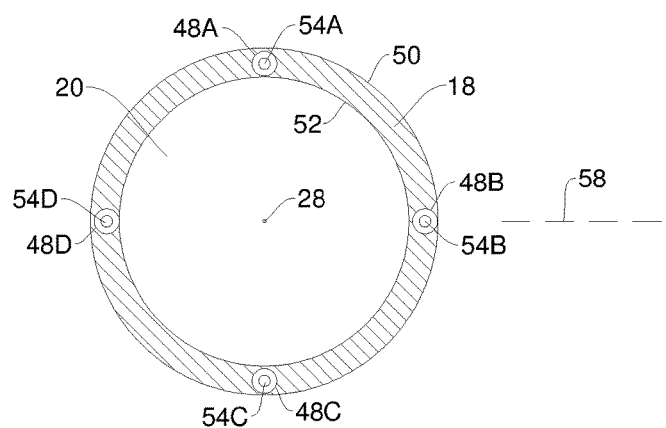
Figure 6:
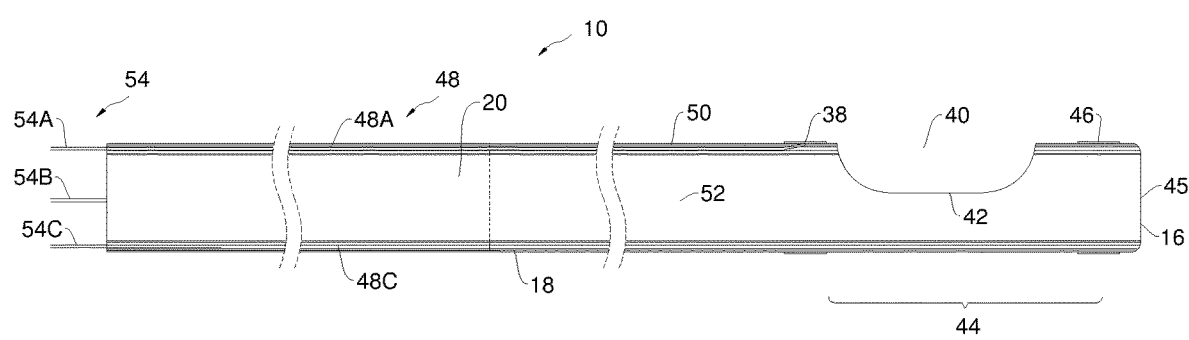
FIG. 6 is a schematic view of the first overtube device viewed from the third angle of view.

With reference to FIG. 4, FIG. 5 and FIG. 6, in an embodiment, there is a plurality of wires (pulling parts) 54 located circumferentially around the longitudinal axis 28. In an embodiment, there are at least two wires (pulling parts) 54 located about 180° apart relative to the longitudinal axis 28. In another embodiment, there are four wires (pulling parts) 54, each within its own respective pulling lumen 48, located approximately 90° apart from each other relative to the longitudinal axis 28. Each of the wires (pulling parts) 54 is in operative connection with the handle 26. In an embodiment, there is a first wire 54A located within a first pulling lumen 48A, a second wire 54B located within a second pulling lumen 48B, a third wire 54C located within a third pulling lumen 48C, and a fourth wire 54D located within a fourth pulling lumen 48D. The first wire 54A and the third wire 54C are configured to control the distal end 16 of the overtube device 10 for movement in a first plane 56. The second wire 54B and the fourth wire 54D are configured to control movement of the distal end 16 of the overtube device 10 in a second plane 58, wherein the second plane 58 is orthogonal to the first plane 56. It can be understood that the first wire 54A and the third wire 54C are disposed to be parallel with each other and the first wire 54A and the third wire 54C define a plane passing thereby, which plane is the first plane 56. Vice versa, the second wire 54B and the fourth wire 54D are disposed to be parallel with each other and the second wire 54B and the fourth wire 54D define a plane passing thereby, which plane is the second plane 58.

It should be noted that when observed in a section view, the second pulling lumen 48B is positioned relative to the longitudinal axis to be at 90 degrees to 180 degrees from the first pulling lumen 48A. The third pulling lumen 48C is positioned relative to the longitudinal axis to be at 90 degrees to 180 degrees from the first pulling lumen 48A. The fourth pulling lumen 48D is positioned relative to the longitudinal axis to be at 90 degrees to 180 degrees from the first pulling lumen 48A.

Evidently, the above-described angle may not be limited to be in a range of 90 to 180 degrees, it may also be in a range of 45 to 180 degrees. Meanwhile, it should be understood that the relative positions shown with the above-described angle may be interpreted based on the clockwise direction in FIG. 5, and the angle may also be interpreted based on the counterclockwise direction in FIG. 5.

With combined reference to FIG. 5, in a specific embodiment, the first pulling lumen 48A, the second pulling lumen 48B, the third pulling lumen 48C and the fourth pulling lumen 48D are uniformly distributed in the circumferential direction, that is, their relative positions are interpreted based on the clockwise direction. The second pulling lumen 48B is positioned relative to the longitudinal axis to be at 90 degrees from the first pulling lumen 48A. The third pulling lumen 48C is positioned relative to the longitudinal axis to be at 180 degrees from the first pulling lumen 48A. The fourth pulling lumen 48D is positioned relative to the longitudinal axis to be at 270 degrees from the first pulling lumen 48A.

Similarly, if their relative positions are interpreted based on the counterclockwise direction, then the fourth pulling lumen 48D is positioned relative to the longitudinal axis to be at 90 degrees from the first pulling lumen 48A. The third pulling lumen 48C is positioned relative to the longitudinal axis to be at 180 degrees from the first pulling lumen 48A. The second pulling lumen 48B is positioned relative to the longitudinal axis to be at 270 degrees from the first pulling lumen 48A.

During operation by a doctor, the distal portion 44 can be bent or moved in the first plane 56 by manipulating the first wire 54A using the handle 26, and the distal portion 44 can be bent or moved in the second plane 58 by manipulating the second wire 54B using the handle 26.

In accordance with an exemplary aspect of the present disclosure, the overtube device 10 supports the passing portion 102 of the endoscope body 101. The overtube device 10 assists the endoscope body 101 to enter the biliary duct or tract more easily and enables the passing portion 102 of the endoscope body 101 to be held in a desired location continuously during the entire endoscopic procedure. This enables the operator grasping the handle 26 to maintain or fix an angle at which the distal end 16 of the overtube device 10 is oriented (i.e., bent) during the procedure to provide the operator with greater control and view of an interior portion of the biliary tract or duct.

While reference is made herein with respect to biliary tracts and biliary ducts, it is to be understood that the overtube device 10 may be used with any endoscope body 101 that enables an operator to view a portion of an interior sidewall of a pulling lumen formed from a tissue, vessel, or medium. Thus, it is to be understood that the overtube device 10 may be applied to any endoscope body 101 that needs additional external support by providing a more rigid material than that which forms the passing portion 102 of the endoscope body 101 carried or disposed within the bore 20 of the overtube device 10. The usage of the overtube device 10 may help to reduce costs during medical procedures since the overtube device 10 allows for a reusable product that can be disinfected and reused between different patients undergoing an endoscopic procedure.

The overtube device 10 enables the operator to provide a better control of the distal end of the endoscope body 101, enabling the distal end of the endoscope body 101 to bend at least 90°, which was previously not possibly realized by the prior surgical instruments. Further, the handle 26 may include a lock to fix the distal end 16 of the overtube device 10 at a desired angle of bend during the medical procedure by locking one of the wires (pulling parts) 54 at a desired tension.

In operation, the overtube device 10 is assembled with the endoscope body 101 by inserting the passing portion 102 of the endoscope body 101 through the bore 20 of the overtube body 18. The passing portion 102 is inserted towards the proximal end 14 of the overtube body 18 and extends out from the distal end 16 of the overtube body 18.

It is to be noted that once the device 10 is assembled onto the endoscope body 101, the distal end 16 may be advanced through a biliary duct or biliary tract. The biliary tract may include naturally occurring curves through which the user or operator needs to navigate. Navigation of the curves of the biliary tract may be accomplished by manipulating the endoscope body 101 through the bore 20 after first adjusting at least one of the wires (pulling parts) 54 by using the handle 26. The manipulation of the wires (pulling parts) 54 causes the distal end 16 to move in the direction of at least one plane. For example, the operator may manipulate the first wire 54A to move the distal end 16 of the overtube body 18 of overtube device 10 in the first plane 56. Optionally, the operator may manipulate the second wire 54B to maneuver the distal end 16 of the overtube body 18 in the second plane 58. The manipulation of the wires (pulling parts) 54 can orient the distal end 16 of the tube 18 at a desired position to allow the sensor 103 carried by the passing portion 102 of the gastroscope body 101 to view outwardly in a radial direction from the opening 40. Optionally, if the sensor 103 is located at the distal end of the passing portion 102 of the endoscope body 101, the sensor 103 may look outwardly from the distal hole 45 to view a portion of the biliary tract or biliary duct.

The overtube device 10 enables the passing portion 102 of the endoscope body 101 to be placed inside the overtube body 18 to allow the endoscope body 101 to visualize both during insertion of the overtube device 10 down the esophagus and into the stomach as well as during inspection of a biliary tract. The wires (pulling parts) 54 enable the overtube device 10 to be moved into position and then the endoscope body 101 is passed outwardly through the distal hole 45, such that the distal end of the endoscope body 101 is able to be inserted into an opening of the biliary duct or tract. Currently, for duodenoscopes, it is a two-step process to inspect the biliary duct or tract. Namely, there is a device that puts the endoscope body 101 in position and then the surgeon utilizes x-rays and other radiation tools to determine that the overtube device 10 is placed in the proper position. The overtube device 10 provided in the embodiments of the present disclosure allows the surgeon to forego the two-step procedure and simply position the endoscope body 101 in the correct position in the biliary tract or biliary duct. Although it is not envisioned that the overtube device 10 be a primary diagnosis tool, it may be a visual inspection tool after it is determined that a prior art device or technique could not be used to grasp whatever foreign object or body is causing the blockage in the biliary tract or biliary duct. Namely, this is enabled by the above overtube device 10 for providing direct visualization down the biliary tract. The device 10 provided in the embodiments of the present disclosure provides a single, disposable tool that can use the endoscope camera (the sensor 103) that has a higher resolution and be able to be placed in a correct position to be moved through the biliary tract. This was previously difficult because of the physical and anatomical placement within the stomach. Thus, by having this overtube device 10 that is able to be controlled and placed into a proper position via wires (pulling parts) 54, the endoscope body 101 may be passed outwardly to more precisely and accurately visualize the biliary tract without needing to perform the two-step process of x-ray and radiation placement, which enables the operation to be more convenient.

With reference to FIG. 7 to FIG. 15, FIG. 7 to FIG. 15 depict a second overtube device 10 provided in an embodiment of the present disclosure. There are similarities between the second overtube device 10 and the first overtube device 10 as shown in FIG. 2 to FIG. 6, and the differences therebetween are mostly to be described in detail below. Apparently, references may be made between the similarities, it is to be noted that relevant technical features of the first overtube device 10 may be combined into the second overtube device 10 without conflict. Vice versa, relevant technical features of the second overtube device 10 may be combined into the first overtube device 10 without conflict.

Similarly, the second overtube device 10 may be used in combination with the endoscope body 101 in FIG. 1, and they form two major portions of the endoscope assembly 100, wherein a passing portion 102 of the endoscope body 101 can slidably pass through a bore 20 of the second overtube device 10 as well.

Figure 7:
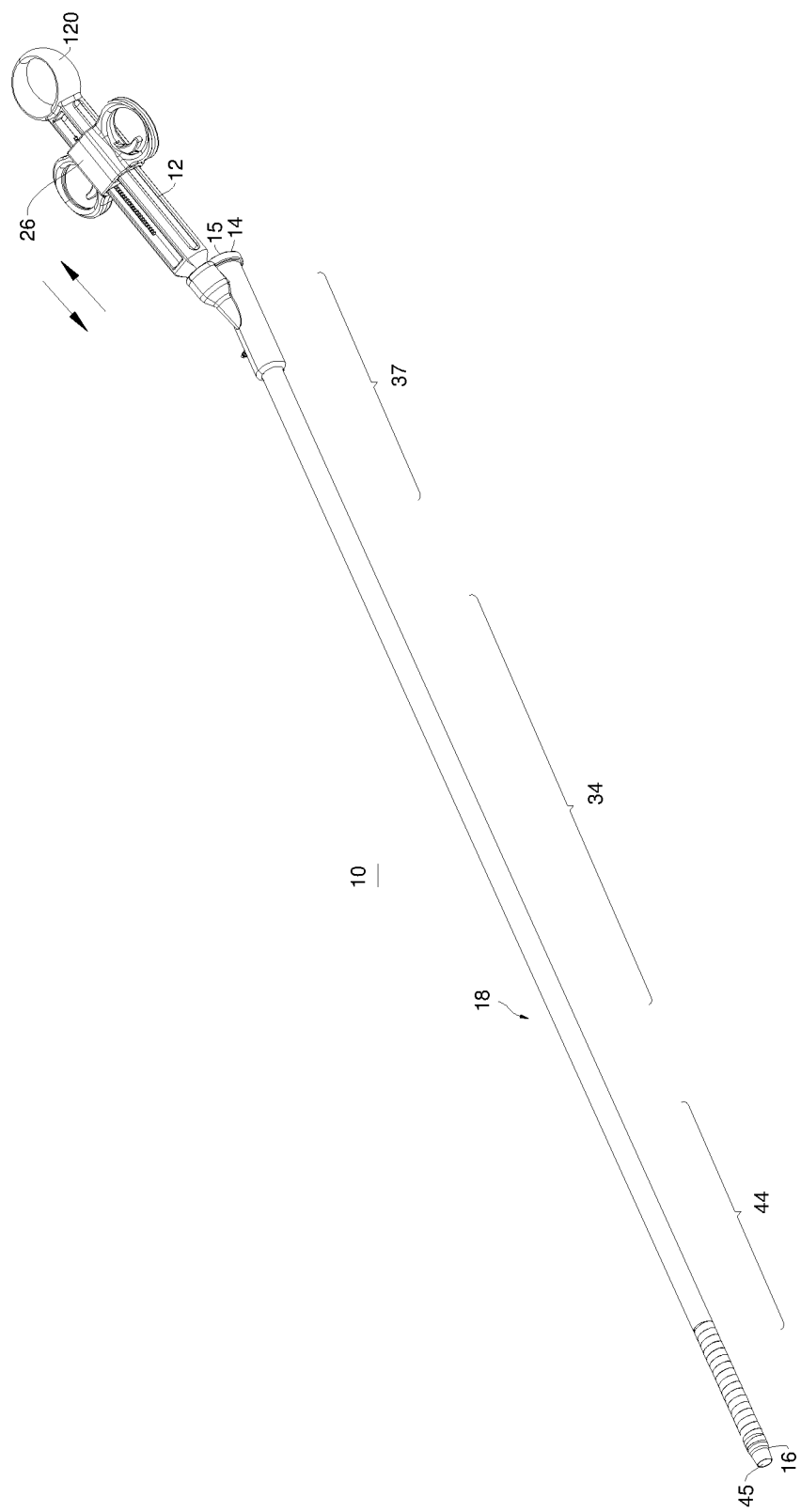
FIG. 7 is an overall view of a second overtube device provided in an embodiment of the present disclosure.
Figure 8:
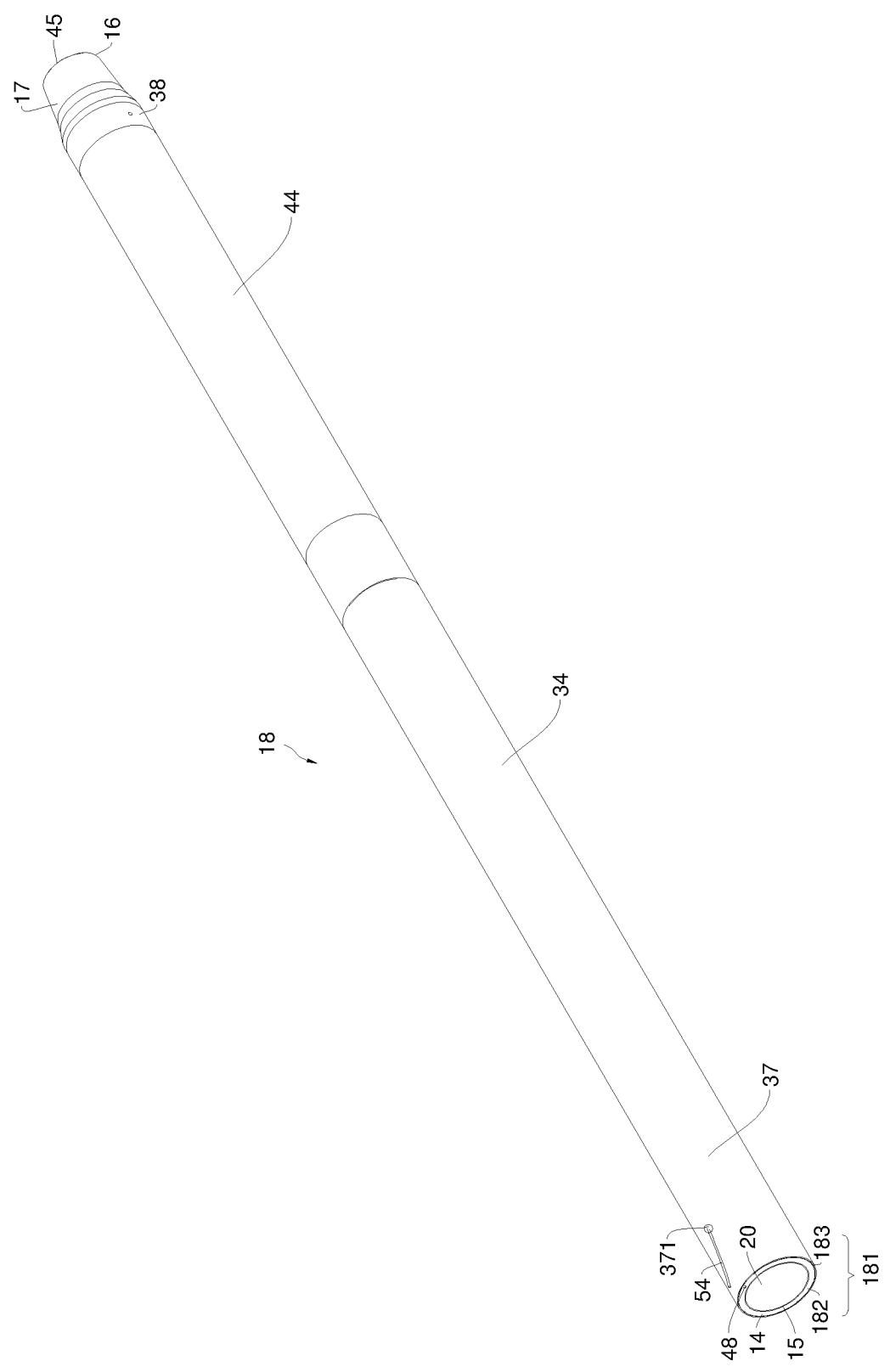
Figure 9:
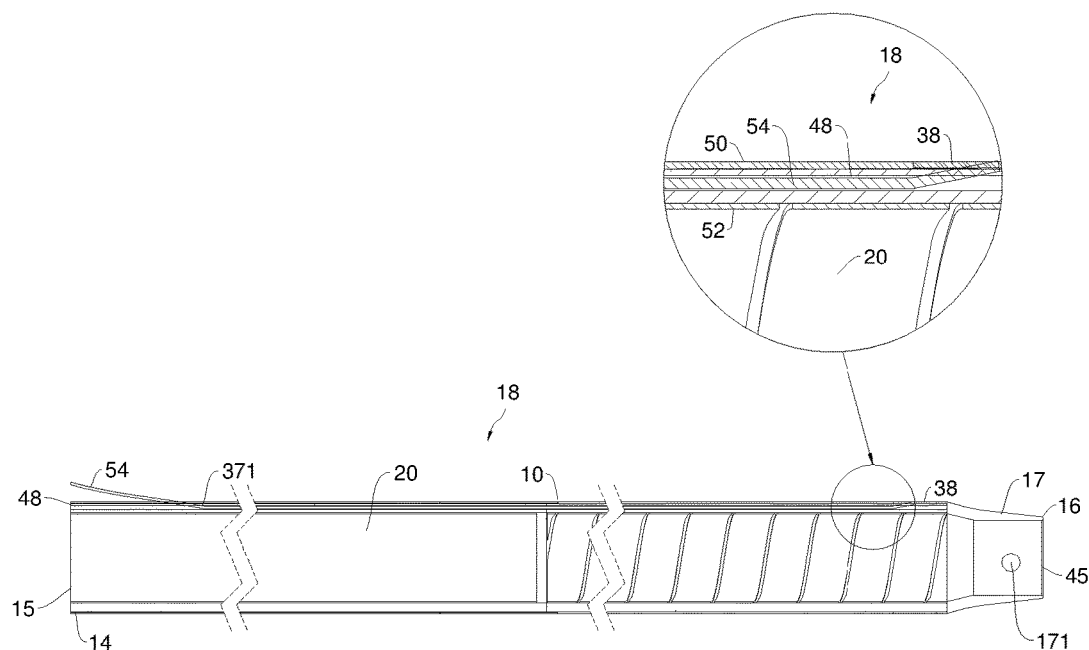
FIG. 9 is a schematic view of the second overtube device viewed from a second angle of view.

With reference to FIG. 7 to FIG. 9, the second overtube device 10 includes an overtube body (which may also be called as an overtube) 18 having a proximal end 14 and a distal end 16, wherein the overtube body 18 is provided with the bore 20, and the bore 20 extends in a direction from the distal end 16 to the proximal end 14 of the overtube body 18, and the bore 20 is configured to allow the passing portion 102 of the endoscope body 101 to pass therethrough.

With reference to FIG. 8 and FIG. 9 in combination, it is to be noted that in this embodiment, the pulling lumen 48 is a round hole and the bore 20 is also a round hole, wherein a diameter of the pulling lumen 48 is smaller than a diameter of the bore 20. In this way, a passing portion 102 having a larger outer diameter can pass through the bore 20, meanwhile, a pulling part (i.e., metal wire) 54 having a smaller outer diameter can pass through the pulling lumen 48. The bore 20 penetrates the proximal end 14 of the overtube body 18 to form a passage hole 15, wherein the passage hole 15 is configured to allow a distal end of the passing portion 102 to be inserted therethrough. The bore 20 penetrates the distal end 16 of the overtube body 18 to form the distal hole 45, wherein the distal hole 45 is configured to allow a distal end of the passing portion 102 to extend out therefrom. In this way, the passing portion 102 of the endoscope body 101 can be inserted into the bore 20 through the passage hole 15 and extend out from the distal hole 45.

In this embodiment, the pulling lumen 48 is formed in the overtube body 48, wherein the pulling lumen 48 extends in a direction from the distal end 16 to the proximal end 14 of the overtube body 18. And the pulling lumen 48 is configured to allow the pulling part 54 to pass therethrough, and a distal end the pulling part 54 is fixed with the distal portion 44 of the overtube body 18, such that the distal portion 44 of the overtube body 18 and the passing portion 102 within the distal portion 44 are bent and/or moved together when the pulling part 54 moves towards the proximal end 14 of the overtube body 18.

With reference to FIG. 8 and FIG. 9 in combination, the overtube body 18 further includes an intermediate portion 34 and a proximal portion 37, wherein the distal portion 44, the intermediate portion 34 and the proximal portion 37 are sequentially connected with each other in the direction from the distal end 16 to the proximal end 14 of the overtube body 18. The pulling lumen 48 does not penetrate the distal end 16 of the overtube body 18, and the pulling lumen 48 penetrates the proximal end 14 of the overtube body 18. The proximal portion 37 is provided with a guide hole 371, wherein the pulling part 54 extends into the pulling lumen 48 via the guide hole 371 provided on a wall of the overtube body 18 close to the proximal end 14 thereof and continuously extends to be fixed with the distal portion 44 of the overtube body 18 until the distal end of the pulling part 54 extends to its farthermost positions. In such manner, when the proximal end of the pulling part 54 is pulled to move towards the proximal end 14 of the overtube body 18, the distal portion 44 of the overtube body 18 may be relatively bent and/or moved. If there is a passing portion 102 passing through the bore 20, when the distal portion 44 is bent, then the passing portion 102 within the distal portion 44 will be bent and/or moved together. It can be understood that a material forming the entirety or a portion of distal portion 44 is relatively soft, thus in a process in which the pulling part 54 is pulled, the distal portion 44 is bent and/or displaced under a force, thereby making the passing portion 102 within the distal portion 44 be bent and/or displaced together therewith.

Figure 10:
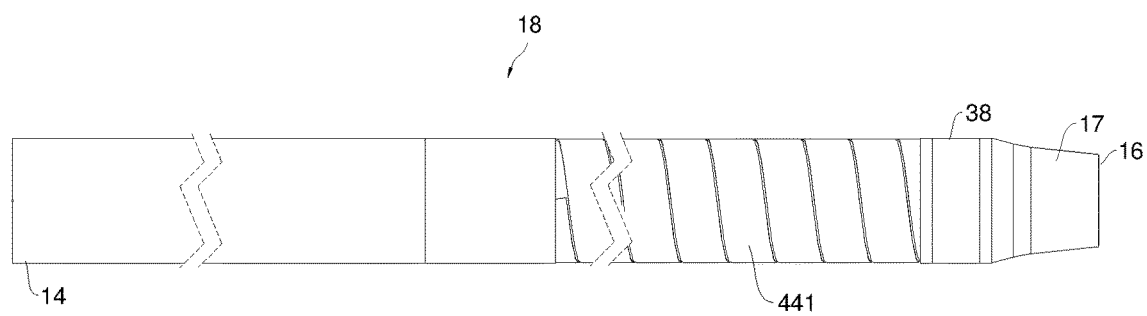
FIG. 10 is a schematic view of the second overtube device viewed from a third angle of view.

With combined reference to FIG. 7 and FIG. 10, an outer surface of the distal portion 44 is formed by coiling a flexible film 441. An inner surface of the distal portion 44 is defined by an inner wall of a tube body, and materials of the flexbile film 441 and the tube body are both Pebax, which facilitates bending of the distal portion 44. The flexible film 441 is a layer of thin film which has a width of 5 mm-10 mm and a thickness of 0.1 mm-0.2 mm. Specifically, the flexible film 441 may be wound and coiled along the axial direction of the overtube body 18 and formed by heat shrinkage (or Pyrocondensation), such that the outer surface of the distal portion 44 is formed. The axial direction of the overtube body 18 may be interpreted as the length direction of the overtube body 18, which is denoted by the arrow in FIG. 7. The heat shrinkage may be realized by blowing. With combined reference to FIG. 10, in an embodiment, after being already coiled on the outer surface, the flexible film 441 is then subjected to reflow so as to be formed. The hardness of the flexible film 441 may be selected to be 35D. In an embodiment, a bending radius of the distal portion is smaller than 4) 28 mm, and the direction of the coiling may be clockwise or counterclockwise.

In this embodiment, each of the intermediate portion 34 and the proximal portion 37 of the overtube body 18 is braided catheter 181, so as to be configured to support the passing portion 102 within the braided catheter 181.

With combined reference to FIG. 8, the material forming the braided catheter 181 has a hardness e, and the material forming the passing portion 102 has a hardness f, where e>f.

It can be understood that the braided catheter 181 can provide strength and hardness to the passing portion 102 passing therethrough, so as to support the passing portion 102.braided catheterbraided catheter Meanwhile, the materials forming the braided catheters of the intermediate portion 34 and the proximal portion 37 may be the same or different.

In this embodiment, the braided catheter 181 includes a tube body 182 and a braided catheter structure 183 formed within the tube body 182 by weaving metal wires. In one molding mode, first the braided catheter structure 183 formed by weaving metal wires is manufactured and molded, then molten material of the tube body is molded onto the braided catheter structure 183 by film covering, such that the braided catheter structure 183 is completely molded in the interior of the tube body 182. In an optional embodiment, the braided catheter structure 182 may be selected as a stainless steel coil. In combination with the above, when each of the distal portion 44, the intermediate portion 34 and the proximal portion 37 is a braided catheter, the materials of the metal wires forming these three portions may be the same or different, and the materials forming the tube bodies of these three portions may be the same or different as well. In general, a medical material is selected for forming the tube body, for example, the material of the tube body 182 may be Thermoplastic polyurethanes, Polytetrafluoroetylene or the like.

Specifically, in this embodiment, the material of the distal portion 44 has a hardness a, the material of the intermediate portion 34 has a hardness b and the material of the proximal portion 37 has a hardness c, where a<b≤c. In other words, the material of the distal portion 44 is relatively softer, while the material of the intermediate portion 34 and the material of the proximal portion 37 are relatively harder, in this way, when the pulling part 54 is pulled, the distal portion 44 is first pulled to be bent. It is to be noted that when the materials forming these three portions are different, connections between the three portions may be realized by using reflow. In general, a length of the distal portion 44 here is in a range of 60 mm-70 mm, a length of the intermediate portion 34 is in a range of 800 mm-900 mm and a length of the proximal portion 37 is in a range of 30 mm-50 mm. Evidently, in actual implementations, the respective lengths of the three portions are not limited to the above ranges.

Meanwhile, in general, a bending diameter of the distal portion of 44 is in a range of 10 mm-30 mm, which is easier for doctors to operate. When bent, it can pass through the blood vessels or tissues of the body more smoothly. Evidently, in actual implementations, the bending diameter is not limited to the above range.

In combination with the above, the overtube device 10 can assists in supporting the passing portion 102 of the endoscope body 101, such that a doctor can very easily place the distal end of the passing portion 102 to a preset position (such as into a biliary duct). Moreover, during entire surgical procedure, the distal end of the passing portion 102 can be kept in the preset position. In this way, the overtube device 10 is reusable, which enables the use costs during the surgical procedure to be relatively lower. Meanwhile, the overtube device 10, in cooperation with the endoscope body 101 can provide a better angle of view to the sensor 103 of the endoscope body 101, such that the doctor can more easily and directly visualize positions requiring diagnosis and treatment.

In this embodiment, the overtube device 10 further includes a pulling part 54, wherein the pulling part 54 can slidably pass through the pulling lumen, and the distal end 16 of the pulling part 54 is fixed with the distal portion 44 of the overtube body 18. such that the distal portion 44 of the overtube body 18 and the passing portion 102 within the distal portion 44 are bent and/or moved together when the pulling part 54 moves towards the proximal end 14 of the overtube body 18.

The pulling part 54 may be selected as a metal wire, an elongated metal wire can not only ensure a degree of strength and hardness, but also a degree of flexibility, and when the distal portion 44 is bent, the metal wire is also bent therewith. With reference to FIG. 8 and FIG. 9 in combination, in this embodiment, one pulling part 54 is provided, that is, only one metal wire is used for pulling. Evidently, in other embodiments, the number of the pulling parts 54 may be at least one, then the number of the pulling lumens 48 is also at least one, for example as shown in FIG. 5, the number of the pulling parts 54 is four, including a first metal wire 54A, a second metal wire 54B, a third metal wire 54C and a fourth metal wire 54D, and in the same way, correspondingly the number of the pulling lumens 48 is also four, including a first pulling lumen 48A, a second pulling lumen 48B, a third pulling lumen 48C and a fourth pulling lumen 48D. In an optional embodiment, at least two pulling lumens 48 are distributed evenly along the circumference of the overtube body 18.

With continued reference to FIG. 8 and FIG. 9, a distal transparent cap 17 is formed at the distal end 16 of the overtube body 18, wherein the distal hole 45 is formed within the distal transparent cap 17. It can be understood that, the distal end 16 of the overtube body may be directly molded into the distal transparent cap 17 when molding the overtube body 18, or the distal end 16 of the overtube body may be molded into the distal transparent cap 17 after the overtube body 18 is molded, the molding modes thereof include, but is not limited to, extrusion molding, welding, adhesion and the like. The distal transparent cap 17 can stably support a space large enough for operations by a doctor, thus shortening the duration of the surgical procedure. Moreover, the doctor can have a wider angle of view via the distal transparent cap 17.

With combined reference to FIG. 9, in order to avoid presence of air at the distal hole 45 at the distal end 16, which causes an obstacle to viewing, in this embodiment, the distal transparent cap 17 is provided with an air hole 171, wherein the air hole 171 penetrates the wall of the distal transparent cap 17 so as to be in communication with the distal hole 45. In this way, the air gathering at the distal hole can be exhausted via the air hole 171, preventing the air gathering here from affecting the doctor's observation and diagnosis.

Optionally, the distal portion 44 of the overtube body 18 is provided with an opening 40, wherein the opening penetrates the wall of the overtube body 18 so as to be in communication with the bore 20, and the opening 40 is configured to allow a sensor 103 at the distal end of the passing portion 102 to capture images or video through the opening 40. As shown in FIG. 3, FIG. 4 and FIG. 6, similar to the structure of the first overtube device 10, the distal portion 44 is provided with the opening 40 to facilitate the sensor 103 to capture images or video. In actual implementation, the opening 40 may extend longitudinally or circumferentially. Evidently, in actual implementation, the opening 40 may not be provided and the sensor 103 can capture images or video via the distal hole 45.

With reference to FIG. 9, the overtube body 18 has an outer surface 50 and an inner surface 52, wherein the bore 20 is defined by the inner surface 52 and the pulling lumen 48 is formed between the outer surface 50 and the inner surface 52. A thickness of the overtube body 18 is defined by a radial distance between the outer surface 50 and the inner surface 52. The pulling part 54 pass through the pulling lumen 48 defined between the outer surface 50 and the inner surface 52. In an embodiment, the pulling lumen 48 is formed in an interlayer of the overtube body 18 when the overtube body is molded, that is, an elongated tube may be mounted in the interlayer of the overtube body 18 when the overtube body is molded, after the molding is completed, the pulling lumen 48 is defined in the interior of the elongated tube. Meanwhile, it is to be noted that the bore 20 is a centre bore, that is, the position of the bore 20 is at a center position of a cross section of the overtube body 18.

Optionally, the distal portion 44 of the overtube body 18 is provided with grooves 36, wherein the grooves 36 are configured to define a bending direction of the overtube body 18. For example, as shown in FIG. 2 of the first overtube device 10, the bending direction of the distal portion 44 is defined by providing the grooves 36, and the number, position, and shape of the grooves 36 are not limited herein.

In an embodiment, the grooves 36 are not in communication with the bore 20. In other words, the grooves 36 are formed in the outer surface 50 of the overtube body 18. The grooves 36 do not penetrate the inner surface 52 of the overtube body 18, that is, the grooves 36 are not in communication with the bore 20 defined by the inner surface 52. In an embodiment, the bore 20 may also be in communication with the grooves 36.

With reference to FIG. 8 and FIG. 9 in combination, the overtube device 10 further includes a first ring 38, wherein the first ring 38 is sleeved on the distal portion 44 of the overtube body 18, and the first ring 38 is configured to be viewable during inspection by a viewing device 200.

For example, during a CT scan or an irradiation of X-ray, the first ring 38 can be identified, which facilitates the doctor to quickly determine the position of the first ring 38, so as to determine the position of the distal portion 44. In an embodiment, the first ring 38 may be fully sleeved on the outer surface 50 of the overtube body 18, covering the outer surface 50 at the corresponding position. Meanwhile, in an embodiment, the first ring 38 is fixedly connected with the distal end of the pulling part 54, for example, the distal end of the pulling part 54 is welded and fixed to the inner wall of the first ring 38.

Figure 11:
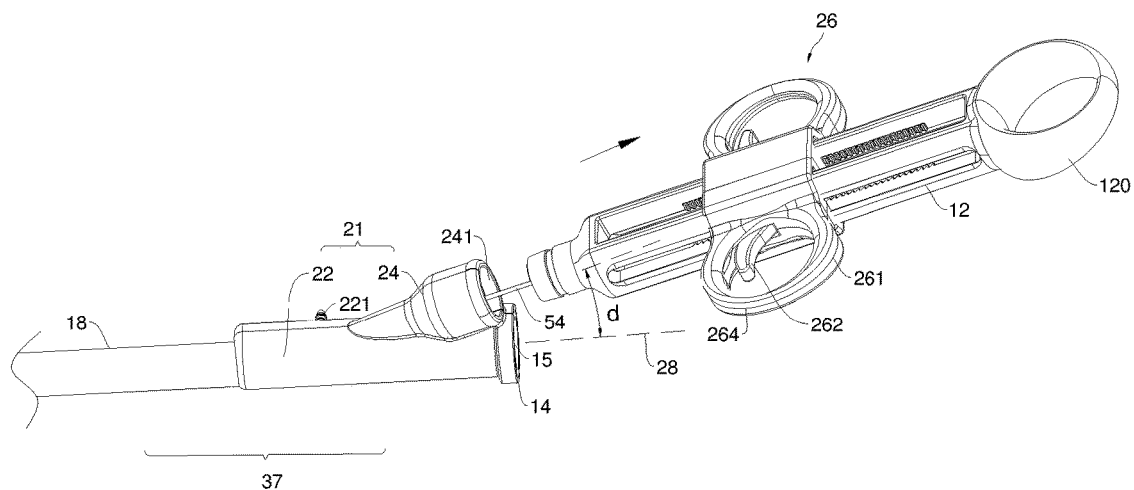
FIG. 11 is a schematic view of relevant components such as a handle and an operation part in the second overtube device.
Figure 12:
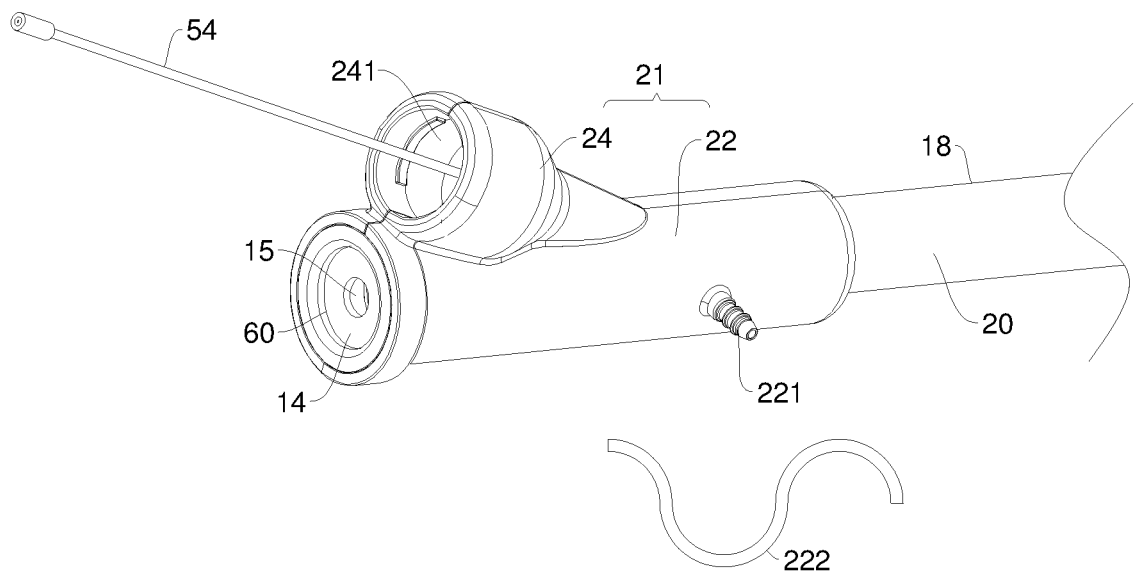
FIG. 12 is a schematic view of the installation part and relevants parts thereof in the second overtube device.

With reference to FIG. 11 and FIG. 12, the overtube device 10 further includes an installation part 21, wherein the installation part 21 includes a connector 24 and a barrel 22 connected with the connector 24, the barrel 22 is sleeved on the proximal portion 37 of the overtube body 18, and the proximal portion 37 is provided with a guide hole 371 (depicted in FIG. 8 and FIG. 9) in communication with the pulling lumen 48, which is configured to guide the pulling part 54 in the pulling lumen 48 to extend out via the barrel 22 and the connector 24. Extending the pulling part 54 out via the connector 24 can facilitate a doctor's operations, moreover, in this embodiment, the connector 24 and the barrel 22 are integratedly formed from a relatively hard material(s), such that the strength and the hardness in the vicinity of the proximal end of the overtube body 18 can be enhanced to some extent.

Referring to FIG. 12, the barrel 22 is connected with a mounting port 221, wherein the mounting port 221 is configured to be connected with a medical tube 222, and the mounting port 221 is in communication with the bore 20. A liquid can be injected into the mounting port 221 via the medical tube 222, the liquid flows into the bore 20 and flows out from the distal hole 45 via the bore 20, so as to flush the distal end 16 of the overtube body 18, or a liquid may be drained using the medical tube 222, such that the liquid at the distal hole 45 can be drained away. An end of the medical tube 222 is connected with a Luer connector 224, so as to improve the convenience of usage.

Figure 13:
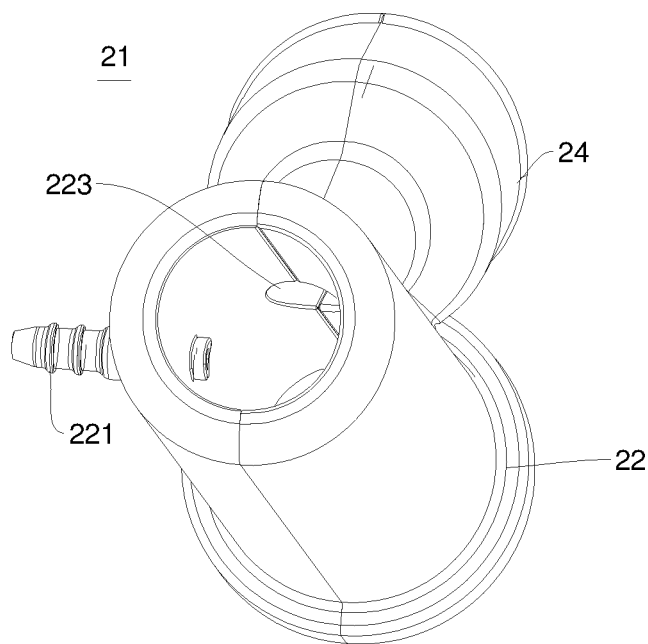
FIG. 13 is a schematic view of the installation part in the second overtube device.

Referring to FIG. 12 and FIG. 13, the installation part 21 includes a communication hole 223 provided in a penetrating manner, wherein an end of the communication hole 223 is in communication with the interior of the barrel 22, and the other end of the communication hole 223 is in communication with the mounting port 241 of the connector 24, such that the pulling part 54 can extend out from the mounting port 241 after passing the communication hole 223.

In order to better control the pulling part 54, in this embodiment, the overtube device 10 further includes an operation part 12 and a handle 26, wherein the operation part 12 is connected with the connector 24, and the handle 26 is connected with the pulling part 54 extending out via the connector 24, and the handle 26 can be slidably connected with the operation part 12 so as to drive the pulling part 54 to move.

Specifically, a distal end of the operation part 12 is mounted in the mounting port 241 of the connector 24, such that when the handle 26 drives the pulling part 54 to move, the distal end of the overtube body 18 is bent or moved.

Figure 14:
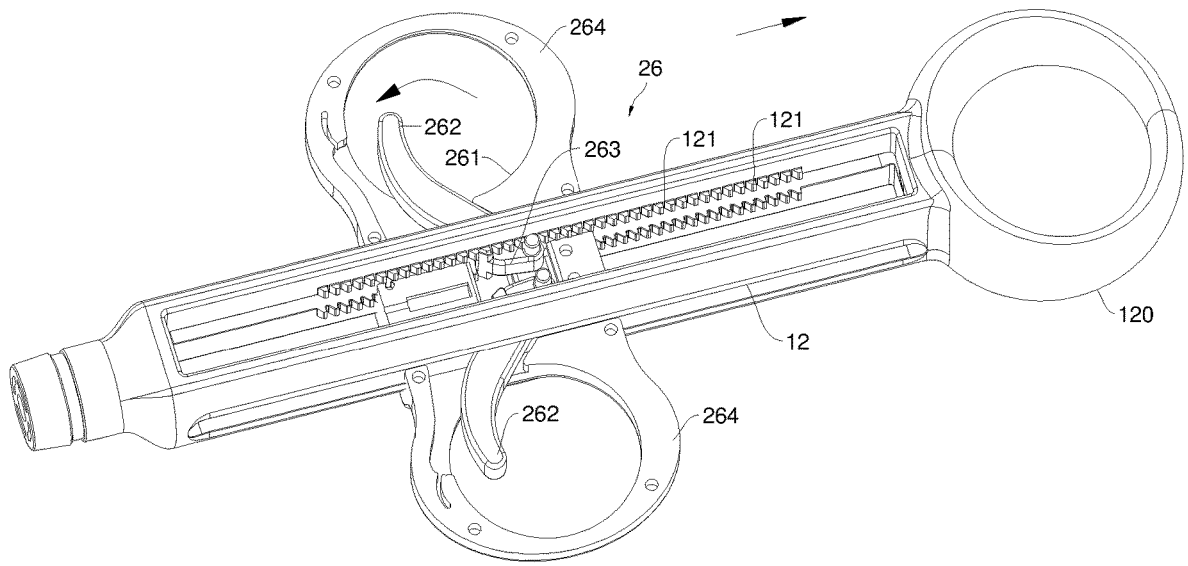
FIG. 14 is a schematic view of the handle and the operation part in the second overtube device.

In actual operations by a doctor, it is usually required to keep the distal portion 44 of the overtube body 18 in a bent state for a certain period of time, therefore, in this embodiment, referring to FIG. 14, the handle 26 is configured to drive the pulling part 54 to move towards the proximal end 14 of the overtube body 18 when sliding relative to the operation part 12 in a preset direction (the direction denoted by the arrow in FIG. 14), and is also configured to be self-locked when sliding relative to the operation part 12 in a direction opposite to the preset direction.

Due to the self-lock of the handle 26, the pulling part 54 can be fixed with the overtube body 18 when it reaches an appropriate position, such that the distal portion 44 of the overtube body 18 can be kept in a bent state for a relatively time.

Figure 15:
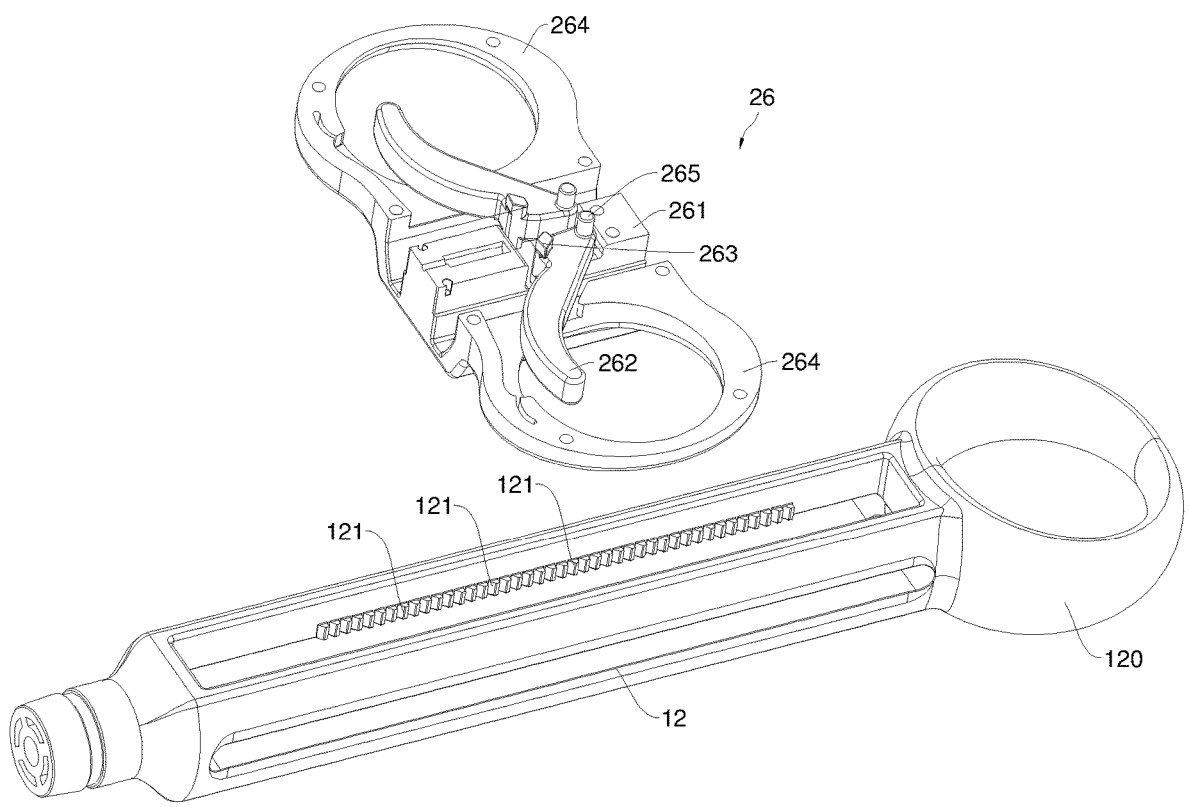
FIG. 15 is a schematic view of the handle and the operation part after being disassembled in the second overtube device.

Specifically, in an embodiment, referring to FIG. 14 and FIG. 15, the handle 26 includes a sliding body 261 and a button 262 rotatably connected with the sliding body 261, wherein the sliding body 261 is slidably connected with the operation part 12, and the pulling part 54 is connected with the sliding body 261. The operation part 12 is provided with a plurality of ratchets 121 arranged in a preset direction in a side-by-side manner, the button 262 is provided with pawls 263, wherein the pawls 263 are configured to cooperate with the ratchets 121 such that the pawls 263 bypass the ratchets 121 to move when the sliding body 261 moves in the preset direction, or the pawls 263 are blocked by the ratchets 121 when the sliding body 261 moves in the direction opposite to the preset direction.

A mechanism formed by the cooperation of the pawls 263 and the ratchets 121 is similar to a ratchet mechanism, and when the sliding body 261 moves in the preset direction, the pawls 263 bypass the ratchets 121 so as to produce a displacement relative to the operation part 12. When the sliding body 261 slides in the direction opposite to the preset direction, each pawl 263 is abutted against and held in an area between the corresponding two adjacent ratchets 121 so as to be blocked by the ratchets 121, such that the sliding body 261 can no longer move. A doctor can operate the button 262 to make the button 262 rotate by a certain angle relative to the sliding body 261, such that the pawls 263 on the button 262 bypass the ratchets 121 to enable the sliding body 261 to continue to move relative to the operation part 12.

With combined reference to FIG. 15, a first finger ring 120 is formed at a proximal end of the operation part 12, and two second finger rings 264 are formed by the sliding body 261. The button 262 is provided with a shaft 265, wherein the shaft 265 is in rotatable connection with the sliding body 261 so as to realize a rotatable connection between the button 262 and the sliding body 261. Meanwhile, the sliding body 261 is further provided thereon with grooves, wherein an elastic piece 266 is mounted in each groove, and the elastic piece 262 is in contact with the respective button 262, and the elastic piece 266 can assist to reset the button 262, such that after the doctor presses the button, once the doctor releases the button, the button 262 can be immediately reset, thereby realizing a quick self-lock.

With combined reference to FIG. 11, the intermediate portion 34 and the proximal portion 37 of the overtube body 18 has a longitudinal axis 28, wherein an included angle d is formed between the preset direction and the longitudinal axis 28, where 15°≤d≤75°, and the angled may be 15°, 30°, 45°, 75° or the like.

With continued combined reference to FIG. 11 and FIG. 12, the overtube device 10 further includes a sealing part 60, the bore 20 penetrates the proximal end 14 of the overtube body 18 to form the passage hole 15, wherein the passage hole 15 is configured to allow insertion of the distal end of the passing portion 102, the sealing part 60 is mounted at the proximal end 14 of the overtube body 18, and the sealing part 60 is configured to seal a gap between the overtube body 18 and the passing portion 102 when the passing portion 102 passes through the bore 20. When the distal portion 44 of the overtube body 18 extends into the stomach of a human body, besides sealing by the sealing part 60, a positive pressure can be formed between the stomach and the inside overtube body 18, which makes the stomach bulge, thus facilitating carrying out the operation.

Material forming the sealing part 60 may be selected as rubber or silicone, when the passing portion 102 of the endoscope body 101 passes through the bore 20, in order to maintain the leakproofness at the proximal end 14 of the overtube body 18, providing the sealing part 60 at this position can ensure this position to be always kept in a sealed environment during passing of the passing portion 102.

In some embodiments:

Referring to FIG. 1, the endoscope assembly 100 shown in FIG. 1 includes an overtube device 10 and an endoscope body 101, wherein the overtube device 10 includes an overtube body 18 having a bore 20 and the overtube body 18 has a distal end 16 and a proximal end 14, the bore 20 extends in a direction from the distal end 16 to the proximal end 14 and penetrates each of the distal end 16 and the proximal end 14. The overtube body 18 includes a distal portion 44, an intermediate portion 34 and a proximal portion 37 which are sequentially connected in the direction from the distal end 16 to the proximal end 14. A passing portion 102 of the endoscope body 101 is an elongated portion, wherein the passing portion 102 pass through the proximal end 14 then is able to slidably pass through the bore 20, the passing portion 102 can extend out from the distal end 16, and a sensor 103 provided at the distal end of the passing portion 102 is configured to capture images or video. The distal portion 44 is bendable so as to drive the passing portion 102 within the distal portion 44 to be bent therewith. A viewing device 200 is configured to scan a human body so as to determine the position of the distal end 16. Two states, i.e., a straight state and a bent state of the distal portion 44 are shown in FIG. 1.

Referring to FIG. 2, the overtube device 10 shown in FIG. 2 includes an overtube body 18 having a bore 20, wherein the overtube body 18 has a distal end 16 and a proximal end 14, the bore 20 extends in a direction from the distal end 16 to the proximal end 14 and penetrates the distal end 16 to form a distal hole 45, and the bore 20 penetrates the proximal end 14 to form a passage hole 15. The overtube body 18 includes a distal portion 44, an intermediate portion 34 and a proximal portion 37 which are sequentially connected in a direction from the distal end 16 to the proximal end 14. The distal portion 44 shown in FIG. 2 shows a bent state. A first ring 38 and a second ring 46 are sleeved outside the distal portion 44, wherein the first ring 38 and the second ring 46 are arranged to be spaced apart from each other, the overtube body 18 arranged between the first ring and the second ring spaced apart is provided with an opening 40, wherein the opening 40 is in communication with the bore 20, and a profile of the opening 40 is defined by an edge 42 of the opening. An outer surface 50 of the overtube body 18 is provided with grooves 36, wherein the grooves 36 are between the first ring 38 and the intermediate portion 34, and the number of the grooves 36 is multiple, including a first groove 36A, a second groove 36B and a third groove 36C, and the positions, number and shape of the grooves 36 are not limited. A midline 35 is defined in the intermediate portion 34, and the intermediate portion 34 and the proximal portion 37 have a longitudinal axis 28. A barrel 22 is sleeved outside the proximal portion 37, a shoulder 32 is defined between a distal end of the barrel 22 and the overtube body 18. The barrel 22 is connected with a connector 24, and the connector 24 is fixed with an operation part 12, wherein a handle 26 is slidably provided on the operation part 12, the sliding directions of the handle 26 is shown with reference to the double-headed arrow, whose extension directions is denoted by the dashed lines. An angle d is formed between the sliding directions and the longitudinal axis 28, wherein the angle d is an acute angle. The handle 26 is configured to control the distal portion 44 to be in a bent state or a straight state.

Referring to FIG. 3, the overtube device 10 shown in FIG. 3 includes an overtube body 18, wherein a first ring 38 and a second ring 46 are sleeved on the distal portion 44 of the overtube body 18, wherein the second ring 46 is close to the distal end 16 of the overtube body 18, and the first ring 38 and the second ring 46 are arranged to be spaced apart from each other. The overtube body 18 is provided with an opening 40, wherein the opening 40 is between the first ring 38 and the second ring 46, a profile of the opening 40 is defined by an edge 42 of the opening, and the opening 40 is in communication with the bore 20 in the overtube body 18. The distal end 16 is provided with a distal hole 45.

Referring to FIG. 4, the overtube body 18 of the overtube device 10 shown in FIG. 4 is provided with a bore 20, a pulling lumen 48 is formed between an outer surface 50 and an inner surface 52 of the overtube body 18, wherein a pulling part 54 passes through the pulling lumen 48. The pulling lumen 48 includes a first pulling lumen 48A, a second pulling lumen 48B, and a fourth pulling lumen 48D, the pulling part 54 includes a first wire 54A, a second wire 54B and a fourth 54D. The first wire 54A passes through the first pulling lumen 48A, the second wire 54B passes through the second pulling lumen 48B, the fourth wire 54D passes through the fourth pulling lumen 48D. A first ring 38 and a second ring 46 are sleeved on the distal portion 44 of the overtube body 18, wherein the second ring 46 is close to the distal end 16 of the overtube body 18, and the first ring 38 and the second ring 46 are arranged to be spaced apart from each other. The overtube body 18 is provided with an opening 40, wherein the opening 40 is between the first ring 38 and second ring 46, a profile of the opening 40 is defined by the edge 42 of the opening, and the opening 40 is in communication with the bore 20 in the overtube body 18. The distal end 16 is provided with a distal hole 45. The overtube body 18 has a longitudinal axis 28.

Referring to FIG. 5, a first pulling lumen 48A, a second pulling lumen 48B, a third pulling lumen 48C and a fourth pulling lumen 48D are formed between an outer surface 50 and an inner surface 52 of the overtube body 18 shown in FIG. 5, wherein the first pulling lumen 48A, the second pulling lumen 48B, the third pulling lumen 48C and the fourth pulling lumen 48D are evenly distributed around the circumference of the overtube body 18, a first wire 54A, a second wire 54B, a third wire 54C and a fourth 54D respectively pass through the first pulling lumen 48A, the second pulling lumen 48B, the third pulling lumen 48C and the fourth pulling lumen 48D. The bore 20 in the overtube body 18 extends along the longitudinal axis 28 of the overtube body. The first wire 54A and the third wire 54C are disposed to be parallel with each other and the first wire and the third wire define a plane passing thereby, which plane is a first plane 56. The second wire 54B and the fourth wire 54D are disposed to be parallel with each other and the second wire and the fourth wire define a plane passing thereby, which plane is a second plane 58.

Referring to FIG. 6, the overtube body 18 of the overtube device 10 shown in FIG. 6 is provided with a bore 20, a pulling lumen 48 is formed between an outer surface 50 and an inner surface 52 of the overtube body 18, wherein a pulling part 54 passes through the pulling lumen 48. The pulling lumen 48 includes a first pulling lumen 48A and a third pulling lumen 48C, the pulling part 54 includes a first wire 54A, a second wire 54B and a third 54C. A first ring 38 and a second ring 46 are sleeved on the distal portion 44 of the overtube body 18, wherein the second ring 46 is close to the distal end 16 of the overtube body 18, and the first ring 38 and the second ring 46 are arranged to be spaced apart from each other. The overtube body 18 is provided with an opening 40, wherein the opening 40 is between the first ring 38 and second ring 46, a profile of the opening 40 is defined by the edge 42 of the opening, and the opening 40 is in communication with the bore 20 in the overtube body 18. The distal end 16 of the overtube body is provided with a distal hole 45. The distal end of the pulling part 54 is fixed with the first ring 38.

Referring to FIG. 7, the overtube body 18 of the overtube device 10 shown in FIG. 7 has a distal end 16 and a proximal end 14, wherein the distal end 16 is provided with a distal hole 45, the proximal end 14 is provided with a passage hole 15. The overtube body 18 includes a distal portion 44, an intermediate portion 34 and a proximal portion 37 which are sequentially connected in a direction from the distal end 16 to the proximal end 14. An operation part 12 is connected outside the proximal portion 37, a handle 26 is slidably connected with the operation part 12, a first finger ring 120 is formed at the proximal end of the operation part 12. Sliding directions of the handle 26 is shown with reference to the double-headed arrow.

Referring to FIG. 8, the overtube body 18 shown in FIG. 8 is provided with a bore 20, a pulling lumen 48, a distal end 16 and a proximal end 14, wherein the bore 20 penetrates the proximal end 14 to form a passage hole 15, and the bore 20 penetrates the distal end 16 to form a distal hole 45. The overtube body 18 includes a distal portion 44, an intermediate portion 34 and a proximal portion 37 which are sequentially connected in a direction from the distal end 16 to the proximal end 14. A first ring 38 is sleeved outside the distal portion 44 and a distal transparent cap 17 is formed at the distal end 16, wherein the distal hole 45 is formed on the distal transparent cap 17. The proximal portion 37 is provided with a guide hole 371 in communication with the pulling lumen 48, wherein the pulling part 54 is configured to extend into the pulling lumen 48 via the guide hole 371 and extend to the first ring 38 so as to be fixedly connected with the first ring 38. Each of the intermediate portion 34 and the proximal portion 37 of the overtube body 18 is a braided catheter 181, wherein the braided catheter 181 includes a tube body 182 and a braided catheter structure 183 formed within the tube body 182.

Referring to FIG. 9 and FIG. 10, the overtube body 18 shown in FIG. 9 is provided with a bore 20, a pulling lumen 48, a distal end 16 and a proximal end 14, wherein the bore 20 penetrates the proximal end 14 to form a passage hole 15, and the bore 20 penetrates the distal end 16 to form a distal hole 45. The overtube body 18 is provided with a guide hole 371, wherein the guide hole 371 is in communication with the pulling lumen 48 such that an external pulling part 54 extends into the pulling lumen 48 via the guide hole 371, and the distal end of the pulling part 54 extends to the vicinity of the distal end 16 of the overtube body 18, and is fixedly connected with a first ring 38 sleeved outside the overtube body 18. A distal transparent cap 17 is formed at the distal end 16 of the overtube body 18, wherein the distal hole 45 is formed on the distal transparent cap 17, moreover, the distal transparent cap 17 is provided with an air hole 171 in communication with the distal hole 45. The overtube body 18 has an outer surface 50 and an inner surface 52, wherein the pulling lumen 48 is formed between the outer surface 50 and the inner surface 52, a pulling part 54 passes through the pulling lumen 48, and the pulling part 54 is fixedly connected with the first ring 38.

Referring to FIG. 11, a proximal end 14 of the overtube body 18 shown in FIG. 10 is provided with a passage hole 15. A barrel 22 is sleeved on a proximal portion 37 of the overtube body 18, wherein the barrel 22 is connected with a connector 24, the barrel 22 and the connector 24 form an installation part 21, and the barrel 22 is provided with a mounting port 221. The connector 24 is provided with a mounting port 241, a pulling part 54 led out form the mounting port 241 is in operative connection with a handle 26, wherein the handle 26 is slidably provided on an operation part 12, and a first finger ring 120 is formed at a proximal end of the operation part 12. The handle 26 includes a sliding body 261 slidably provided on an operation part 12 and a button 262 rotatably connected with the sliding body 261, wherein the sliding body 261 includes two second finger rings 264. The handle 26 is configured to drive the pulling part 54 to slide in a preset direction when sliding relative to the operation part 12 in a preset direction, and the handle 26 is also configured to be self-locked when sliding in a direction opposite to a preset direction and be unlocked by the button 262. The preset direction is shown by the arrow in the figure and denoted by the dashed line, wherein an included angle d is formed between the preset direction and a longitudinal axis 28 of the overtube body 18, and the angle d is an acute angle.

Referring to FIG. 12, a barrel 22 is sleeved outside the overtube body 18 shown in FIG. 12, wherein the barrel 22 is connected with a connector 24, the barrel 22 and the connector 24 form an installation part 21, and the barrel 22 and the connector 24 are integratedly formed. The barrel 22 is provided with a mounting port 221, wherein the mounting port 221 is configured to be connected with a medical tube 222, and a liquid can be injected into or drained from the bore 20 of the overtube body 18 via the medical tube 222. The connector 24 is provided with a mounting port 241, wherein a pulling part 54 is led out form the mounting port 241. A proximal end 14 of the overtube body 18 is provided with a passage hole 15, wherein a sealing part 60 is provided at a position covering the passage hole 15, and the sealing part 60 is configured to seal a gap between a passing portion and a passage hole when the passing portion 102 of an endoscope body 101 passes through the passage hole 15.

Referring to FIG. 13, the installation part 21 shown in FIG. 13 includes a connector 24 and a barrel 22 which are integratedly formed, wherein the barrel 22 is provided with a mounting port 221, and the mounting port 221 is in communication with the interior of the barrel 22, and the installation part 21 is provided with a communication hole 223 for communicating the interior of the barrel 22 with the interior of the connector 24.

Referring to FIG. 14, a first finger ring 120 is formed at a proximal end of the operation part 12 shown in FIG. 14, and a plurality of ratchets 121 spaced apart in a side-by-side manner are provided in a preset direction (denoted by the straight arrow). The operation part 12 has a hollow intermediate region where a slideway is provided. The handle 26 includes a sliding body 261 and a button 262, wherein a slidable connection between the sliding body 261 and the operation part 12 is achieved by the slideway. The button 262 has an end rotatably connected with the sliding body and the other end located in within a second finger ring 262 which is formed by the sliding body 261. The button 262 is provided with pawls 263, wherein the pawls 263 are configured to cooperate with the ratchets 121 such that the pawls 263 bypass the ratchets 121 to continue to move when the sliding body 261 moves relative to the operation part 12 in the preset direction, and the pawls 263 are blocked and stopped between the two corresponding adjacent ratchets 121 when the sliding body 261 moves relative to the operation part 12 in a direction opposite to the preset direction. When the button 262 rotates relative to the sliding body 261 in the direction denoted by the curved arrow in the figure, the pawls 263 can bypass the ratchets 121 such that the sliding body 261 can move relative to the operation part 12 in the direction opposite to the preset direction.

Referring to FIG. 15, a first finger ring 120 and a plurality of ratchets 121 which are spaced apart are formed at a proximal end of the operation part 12 shown in FIG. 15. The handle 26 includes a sliding body 261, a button 262, pawls 263, a shaft 265 and two second finger rings 264 formed at two sides of the sliding body 261. An end of the button 262 is provided with the shaft 265 and the pawls 263, the shaft 265 is in a rotatable connection with the sliding body 261 around an axis of the shaft, the pawls 263 and the ratchets 121 are configured to be used in cooperation, and the other end of the button 262 is in the interior of the corresponding second finger ring 264.

Various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The articles "a" and "an," as used herein in the specification and in the claims, unless clearly indicated to the contrary, should be understood to mean "at least one." The phrase "and/or," as used herein in the specification and in the claims (if at all), should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Spatially relative terms, such as "under", "below", "lower", "over", "upper", "above", "behind", "in front of", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal", "lateral", "transverse", "longitudinal", and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed herein could be termed a second feature/element, and similarly, a second feature/element discussed herein could be termed a first feature/element without departing from the teachings of the present disclosure.

An embodiment is an implementation or example of the present disclosure. Reference in the specification to "an embodiment," "one embodiment," "some embodiments," "an embodiment," or "other embodiments," or the like, means that a particular feature, structure, or characteristic described in connection with the embodiments is included in at least some embodiments, but not necessarily all embodiments, of the present disclosure. The various appearances "an embodiment," "one embodiment," "some embodiments," "an embodiment," or "other embodiments," or the like, are not necessarily all referring to the same embodiments.

If this specification states a component, feature, structure, or characteristic "may", "might", or "could" be included, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

As used herein in the specification and claims, including as used in the embodiments and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Additionally, any method of performing the present disclosure may occur in a sequence different than those described herein. Accordingly, no sequence of the method should be read as a limitation unless explicitly stated. It is recognizable that performing some of the steps of the method in a different order could achieve a similar result.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures.

In the foregoing description, certain terms have been used for brevity, clarity, and understanding. No unnecessary limitations are to be implied therefrom beyond the requirement of the prior art because such terms are used for descriptive purposes and are intended to be broadly construed.

Moreover, the description and illustration of various embodiments of the disclosure are examples and the disclosure is not limited to the exact details shown or described.

INDUSTRIAL APPLICABILITY

In summary of the above, the present disclosure provides an overtube device and an endoscope assembly, the overtube device has relatively low use costs, and the overtube device can assist a doctor to more easily operate an endoscope body to pass through tissues more smoothly to reach a preset position.

What is claimed is:

1. An overtube device comprising:
an overtube body having a proximal end and a distal end, the overtube body having an outer surface and an inner surface that defines a bore extending along a longitudinal axis; the overtube body has a thickness measured radially relative to the longitudinal axis between the outer surface and an inner surface; and
a first pulling lumen formed in the overtube body between the inner surface and the outer surface, wherein the first pulling lumen has a diameter smaller than a diameter of the bore; wherein the first pulling lumen is adapted to receive a component therein that effectuates movement of the overtube body at the distal end such that the overtube device may be installed over a passing portion of an endoscope body to structurally support the passing portion,
wherein the overtube body is further provided with a guide hole which is in communication with the first pulling lumen and is configured to guide a pulling part in the first pulling lumen.

2. The overtube device of claim 1, further comprising:
at least one groove formed in the outer surface of the overtube body, wherein the at least one groove is located at the distal end with respect to a midline of the overtube body.

3. The overtube device of claim 1, further comprising:
a second pulling lumen formed in the overtube body between the inner surface and the outer surface, wherein the second pulling lumen has a diameter smaller than the diameter of the bore;
wherein, when viewed in cross section, the second pulling lumen is positioned relative to the longitudinal axis to be at 90 degrees to 180 degrees from the first pulling lumen.

4. The overtube device of claim 3, further comprising:
a third pulling lumen formed in the overtube body between the inner surface and the outer surface, wherein the third pulling lumen has a diameter smaller than the diameter of the bore,
wherein, when viewed in cross section, the third pulling lumen is positioned relative to the longitudinal axis to be at 90 degrees to 180 degrees from the first pulling lumen.

5. The overtube device of claim 4, further comprising:
a fourth pulling lumen formed in the overtube body between the inner surface and the outer surface, wherein the fourth pulling lumen has a diameter smaller than the diameter of the bore,
wherein, when viewed in cross section, the fourth pulling lumen is positioned relative to the longitudinal axis to be at 90 degrees to 180 degrees from the first pulling lumen.

6. The overtube device of claim 1, further comprising:
a ring surrounding the outer surface of the overtube body at the distal end of the overtube body that is adapted to viewable during inspection by a viewing device.

7. The overtube device of claim 1, further comprising:
an edge of the overtube body, offset parallel to the longitudinal axis and defining a radially aligned opening adapted to permit a portion of the endoscope body that the overtube body shields or shrouds, to view outwardly therethrough.

8. The overtube device of claim 1, further comprising:
an edge of the overtube body circumscribing the longitudinal axis, with the edge defining a longitudinally aligned opening adapted to permit a portion of the endoscope body that the overtube body shields or shrouds, to view outwardly therethrough.

9. The overtube device of claim 1, wherein the overtube body is more rigid than the passing portion of the endoscope body positioned within the bore.

10. An overtube device comprising:
a overtube body having a proximal end and a distal end, wherein the overtube body is provided with a bore extending in a direction from the distal end of the overtube body to the proximal end of the overtube body, and the bore is configured to allow a passing portion of an endoscope body to pass therethrough; and
a pulling lumen formed in the overtube body, wherein the pulling lumen extends in a direction from the distal end of the overtube body to the proximal end of the overtube body, and the pulling lumen is configured to allow a pulling part to pass therethrough, a distal end of the pulling part is fixed with a distal portion of the overtube body such that the distal portion of the overtube body and the passing portion within the distal portion are bent and/or moved together when the pulling part moves towards the proximal end of the overtube body, and a proximal portion is provided with a guide hole in communication with the pulling lumen, and the guide hole is configured to guide the pulling part in the pulling lumen.

11. The overtube device of claim 10, wherein an outer surface of the distal portion is formed by coiling a flexible film.

12. The overtube device of claim 11, wherein the flexible film is wound and coiled along an axial direction of the overtube body and is subjected to heat shrinkage, such that the outer surface of the distal portion is formed.

13. The overtube device of claim 10, wherein each of the intermediate portion and the proximal portion of the overtube body is a braided catheter, so as to support the passing portion within the braided catheter.

14. The overtube device of claim 13, wherein the braided catheter includes a tube body and a braided catheter structure formed within the tube body by weaving metal wires.

15. The overtube device of claim 10,
wherein the overtube device further comprises the pulling part, and the pulling part can slidably pass through the pulling lumen.

16. The overtube device of claim 10,
wherein the overtube body further comprises an intermediate portion, wherein the distal portion, the intermediate portion and the proximal portion are sequentially connected with each other in the direction from the distal end to the proximal end of the overtube body;
material of the distal portion has a hardness a;
material of the intermediate portion has a hardness b;
material of the proximal portion has a hardness c;
a<b≤c.

17. The overtube device of claim 10, wherein the overtube device further comprises an installation part, the installation part comprises a connector and a barrel connected with the connector, the connector is sleeved on the proximal portion of the overtube body, and the guide hole is further configured to guide the pulling part in the pulling lumen to extend out via the barrel and the connector.

18. The overtube device of claim 17, wherein the barrel is connected with a mounting port, the mounting port is configured to be connected with a medical tube and the mounting port is in communication with the bore.

19. The overtube device of claim 17, wherein the overtube device further comprises an operation part and a handle, the operation part is connected with the connector, and the handle is connected with the pulling part extending out via the connector, and the handle can be slidably connected with the operation part so as to drive the pulling part to move.

20. The overtube device of claim 19, wherein the handle is configured to drive the pulling part to move towards the proximal end of the overtube body when the handle slides relative to the operation part in a preset direction, and the handle is also configured to be self-locked when sliding relative to the operation part in a direction opposite to the preset direction.

21. The overtube device of claim 20, wherein the handle includes a sliding body and a button rotatably connected with the sliding body, the sliding body is slidably connected with the operation part, and the pulling part is connected with the sliding body;
the operation part is provided with a plurality of ratchets arranged in a preset direction and in a side-by-side manner, the button is provided with pawls, wherein the pawls are configured to cooperate with the ratchets such that the pawls bypass the ratchets to move when the sliding body moves in the preset direction, or the pawls are blocked by the ratchets when the sliding body moves in the direction opposite to the preset direction.

22. The overtube device of claim 20, wherein the intermediate portion and the proximal portion of the overtube body have a longitudinal axis, an included angle d is formed between the preset direction and the longitudinal axis, where $15°≤d≤75°$.

23. The overtube device of claim 10, wherein the bore penetrates the distal end of the overtube body to form a distal hole, wherein the distal hole is configured to allow a distal end of the passing portion to extend out therefrom.

24. The overtube device of claim 23, wherein a distal transparent cap is formed at the distal end of the overtube body, and the distal hole is formed within the distal transparent cap.

25. The overtube device of claim 10, wherein the overtube device further comprises a first ring, the first ring is sleeved on the distal portion of the overtube body, and the first ring is configured to be viewable during inspection by a viewing device.

26. The overtube device of claim 10, wherein the overtube device further comprises a sealing part, the bore penetrates the proximal end of the overtube body to form a passage hole, wherein the passage hole is configured to allow insertion of a distal end of the passing portion, the sealing part is mounted at the proximal end of the overtube body, and the sealing part is configured to seal a gap between the overtube body and the passing portion when the passing portion passes through the bore.

27. An endoscope assembly comprising the endoscope body and the overtube device of claim 10, wherein the passing portion of the endoscope body can slidably pass through the bore.

28. The endoscope assembly of claim 27, further comprising a catheter and a balloon connected with the catheter, wherein the balloon and the catheter are configured to assists in pulling the overtube body.

29. The endoscope assembly of claim 27, wherein each of the intermediate portion and the proximal portion of the overtube body is a braided catheter, material of the braided catheter has a hardness e, and material of the passing portion has a hardness f, where e>f.

* * * * *